(12) United States Patent
Bao et al.

(10) Patent No.: US 12,019,372 B2
(45) Date of Patent: Jun. 25, 2024

(54) DIRECTLY PHOTO-PATTERNABLE, STRETCHABLE, ELECTRICALLY CONDUCTIVE POLYMER

(71) Applicant: THE BOARD OF TRUSTEES OF THE LELAND STANFORD JUNIOR UNIVERSITY, Stanford, CA (US)

(72) Inventors: Zhenan Bao, Stanford, CA (US); Yuanwen Jiang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 705 days.

(21) Appl. No.: 16/867,435

(22) Filed: May 5, 2020

(65) Prior Publication Data

US 2020/0401042 A1   Dec. 24, 2020

Related U.S. Application Data

(60) Provisional application No. 62/845,463, filed on May 9, 2019.

(51) Int. Cl.
*G03F 7/032* (2006.01)
*A61B 5/282* (2021.01)
(Continued)

(52) U.S. Cl.
CPC .............. *G03F 7/032* (2013.01); *A61B 5/282* (2021.01); *A61B 5/296* (2021.01); *C08G 81/024* (2013.01);
(Continued)

(58) Field of Classification Search
CPC ....................................................... H01B 1/27
See application file for complete search history.

(56) References Cited

U.S. PATENT DOCUMENTS 7,608,342 B2 * 10/2009 Zhong .................... H01B 1/127
427/372.2
7,842,196 B2 * 11/2010 Yoshida .................. C08L 65/00
252/500

(Continued)

FOREIGN PATENT DOCUMENTS

CN  107805310 A  *  3/2018  .......... C08F 283/065
CN  110256694 A  *  9/2019
(Continued)

OTHER PUBLICATIONS

Machine translation of CN-107805310-A (no date).*
(Continued)

*Primary Examiner* — Amanda C. Walke
(74) *Attorney, Agent, or Firm* — Foley & Lardner LLP

(57) ABSTRACT

One or more embodiments relate to an electrically conductive polymer with a crosslinkable additive. The electrically conductive polymer is a directly photopatternable Poly(3,4-ethylenedioxythiophene):poly(styrenesulfonate) PEDOT: PSS film with cross-linked network made of a plurality of monomers. The directly photopatternable PEDOT:PSS film PEDOT as such has a better conductivity and stretchability compared to its other counterparts. The directly photopatternable PEDOT:PSS film can further be supplemented with poly(ethylene glycol) diacrylate (PEGDA) which can help with the removal of PSS. Advantageously, the PEGDA supplemented PEDOT:PSS film can exhibit a larger charge storage capacity.

9 Claims, 27 Drawing Sheets

(51) Int. Cl.
    *A61B 5/296*     (2021.01)
    *C08G 81/02*     (2006.01)
    *C09D 5/24*     (2006.01)
    *C09D 187/00*     (2006.01)
    *G03F 7/16*     (2006.01)
    *G03F 7/20*     (2006.01)
    *G03F 7/26*     (2006.01)
    *H01B 1/12*     (2006.01)
    *H01B 13/00*     (2006.01)

(52) U.S. Cl.
    CPC ............ *C09D 5/24* (2013.01); *C09D 187/005* (2013.01); *G03F 7/162* (2013.01); *G03F 7/2002* (2013.01); *G03F 7/2041* (2013.01); *G03F 7/26* (2013.01); *H01B 1/127* (2013.01); *H01B 13/0036* (2013.01); *A61B 2562/125* (2013.01)

(56) References Cited

U.S. PATENT DOCUMENTS

| 10,109,386 | B2* | 10/2018 | Mallires | H01B 1/127 |
|---|---|---|---|---|
| 2006/0062958 | A1* | 3/2006 | Yoshida | H01G 9/042 |
| | | | | 428/64.4 |
| 2013/0171338 | A1* | 7/2013 | Pan | C08G 61/126 |
| | | | | 252/500 |
| 2019/0062482 | A1* | 2/2019 | Highgate | C08F 273/00 |
| 2019/0390068 | A1* | 12/2019 | Feig | A61L 27/16 |
| 2022/0293859 | A1* | 9/2022 | Liu | H01L 51/055 |

FOREIGN PATENT DOCUMENTS

| JP | 2017086824 A * | 5/2017 | |
|---|---|---|---|
| WO | WO-2007061559 A2 * | 5/2007 | ............. H01B 1/127 |
| WO | WO-2010058108 A1 * | 5/2010 | ............... B64G 1/44 |
| WO | WO-2015088999 A1 * | 6/2015 | ........... C08G 61/126 |
| WO | WO-2016101044 A1 * | 6/2016 | ......... C08G 73/0266 |
| WO | WO-2017153705 A1 * | 9/2017 | ............... C08F 2/16 |
| WO | WO-2017/191932 A1 | 11/2017 | |
| WO | WO-2022159512 A1 * | 7/2022 | |

OTHER PUBLICATIONS

Machine translation of JP-2017086824-A (no date).*
Khodagholy et al., "Highly Conformable Conducting Polymer Electrodes for In Vivo Recordings", Advanced Materials, 23, H268-H272 (2011).
Khodagholy et al., "NeuroGrid: recording action potentials from the surface of the brain", Nature Neuroscience, vol. 18, No. 2, Feb. 2015, pp. 310-315.
Rivnay et al., "Next-generation probes, particles, and proteins for neural interfacing", Science Advances, 3:e1601649, Jun. 9, 2017, pp. 1-20.

* cited by examiner

DIRECTLY PHOTO-PATTERNABLE, STRETCHABLE, ELECTRICALLY CONDUCTIVE POLYMER

CROSS-REFERENCE TO RELATED PATENT APPLICATIONS

This application claims priority from U.S. Provisional Application No. 62/845,463, filed May 9, 2019, the contents of which are incorporated herein by reference in their entirety.

TECHNICAL FIELD

The present embodiments relate generally to stretchable conductive organic materials, and more particularly to stretchable conductive polymers.

BACKGROUND

Poly(3,4-ethylenedioxythiophene):poly(styrenesulfonate) (PEDOT:PSS) is by far the most widely considered electrically conductive polymer, given its high conductivity, intrinsic stretchability, and good stability. A range of applications in wearable and implantable electronics are proposed based on PEDOT:PSS. Nevertheless, current fabrication of PEDOT:PSS electrodes can be done through a tedious indirect patterning method involving the formation of an etch mask and a subsequent dry etching process. Attempts are made for direct photo-patterning of PEDOT:PSS, but a resulting film either loses its high conductivity or did not yield good stretchability. Therefore, it is desired to develop directly photo-patternable PEDOT:PSS while preserving its conductivity and stretchability. It is against this background that a need arose to develop the embodiments described herein.

SUMMARY

One or more embodiments relate to a One or more embodiments relate to an electrically conductive polymer with a crosslinkable additive. The electrically conductive polymer is directly photopatternable Poly(3,4-ethylenedioxythiophene):poly(styrenesulfonate) PEDOT:PSS film with cross-linked network made of a plurality of monomers. The directly photopatternable PEDOT:PSS film PEDOT as such has a better conductivity and stretchability compared to its other counterparts.

The directly photopatternable PEDOT:PSS film can further be supplemented with poly(ethylene glycol) diacrylate (PEGDA) which can help with the removal of PSS. Advantageously, the PEGDA supplemented PEDOT:PSS film can exhibit a larger charge storage capacity.

BRIEF DESCRIPTION OF THE DRAWINGS

These and other aspects and features of the present embodiments will become apparent to those ordinarily skilled in the art upon review of the following description of specific embodiments in conjunction with the accompanying figures, wherein.

DETAILED DESCRIPTION

Figure 1:
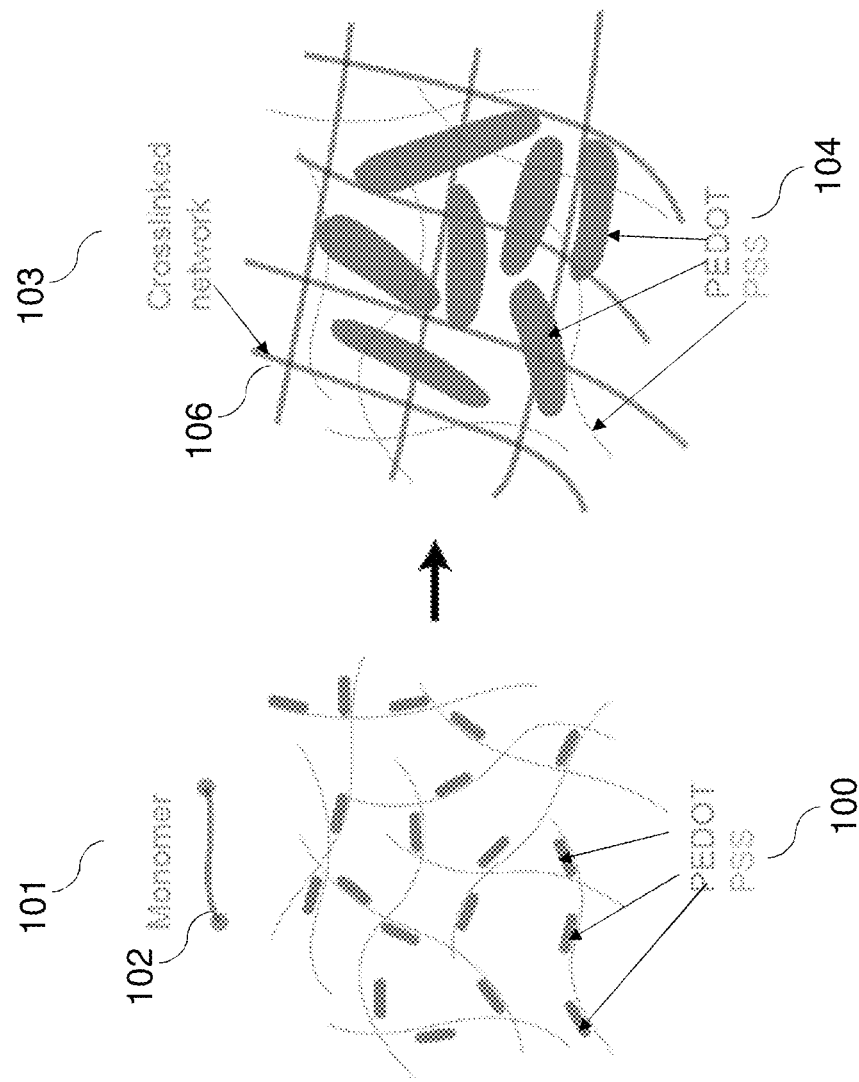
FIG. 1 is a diagram illustrating an existing type of photopatternable Poly(3,4-ethylenedioxythiophene):poly(styrenesulfonate) (PEDOT:PSS) polymer structure and a PEDOT:PSS polymer structure with a cross-linked network, according an embodiment of the present disclosure.

The present embodiments will now be described in detail with reference to the drawings, which are provided as illustrative examples of the embodiments so as to enable those skilled in the art to practice the embodiments and alternatives apparent to those skilled in the art. Notably, the figures and examples below are not meant to limit the scope of the present embodiments to a single embodiment, but other embodiments are possible by way of interchange of some or all of the described or illustrated elements. Moreover, where certain elements of the present embodiments can be partially or fully implemented using known components, only those portions of such known components that are necessary for an understanding of the present embodiments will be described, and detailed descriptions of other portions of such known components will be omitted so as not to obscure the present embodiments. Embodiments described as being implemented in software should not be limited thereto, but can include embodiments implemented in hardware, or combinations of software and hardware, and vice-versa, as will be apparent to those skilled in the art, unless otherwise specified herein. In the present specification, an embodiment showing a singular component should not be considered limiting; rather, the present disclosure is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present embodiments encompass present and future known equivalents to the known components referred to herein by way of illustration.

Structure-engineered stretchable inorganic materials have been demonstrated for various bioelectronic applications. On the other hand, intrinsically stretchable and conductive organic materials have been underdeveloped. Indeed, organic conductors as represented by PEDOT:PSS possess several important features that are particularly beneficial to a biointerface. First, PEDOT:PSS has a much lower Young's modulus than inorganic counterparts, which is of importance to forming intimate contacts with underlying soft and curvilinear tissues with less foreign body responses. Secondly, PEDOT:PSS has a dual conduction ability to transport both electrons and ions, which matches well to ionic conduction in a biological tissue. In conjunction with a large volumetric capacitance of PEDOT:PSS, its overall interfacial impedance is significantly lower than those from inorganic/tissue interfaces. Finally, PEDOT:PSS allows a high-resolution multimodal interrogation of a biological system due to its simultaneously high conductivity, stretchability, transparency, patternability, and low impedance that other systems cannot readily achieve. For gold or silver, their optical transparency can be improved with a holey design. For carbon, direct photolithography and good stretchability cannot be readily achieved.

Stretchable PEDOT:PSS is a recent topic and comparative strategies involve plasticizers that can change the PEDOT:PSS morphology and reduce its material stiffness. For example, an ionic liquid can be used as a plasticizer and de-dopant that simultaneously promote the conductivity and stretchability of PEDOT:PSS. After immersing in water to remove the ionic liquid, a hydrogel form of PEDOT:PSS is applied for sciatic nerve stimulation and cardiac mapping. Nevertheless, due to the removal of the plasticizer and de-dopant, the as-prepared PEDOT:PSS can undergo degradation of its conductivity and stretchability over time, especially under a physiological condition.

In order to achieve an aqueously stable, highly conductive and stretchable PEDOT:PSS system with photo-patternability, it is proposed that a photo-crosslinkable additive can serve as a long-lasting plasticizer and de-dopant for PEDOT:PSS. Therefore, it is proposed to introduce photo-responsive functional groups to PEDOT:PSS additives that can later be cross-linked to form a permanent cross-linked network. Importantly, the end result is useful for bioelectronic applications, as well as for various other stretchable devices and circuits.

Some embodiments of this disclosure are directed to a photo-curable composition including an electrically conductive polymer, such as PEDOT:PSS, supplemented with a crosslinkable additive that allows direct photo-patterning while providing a high electrical conductivity, a high stretchability, and a high water stability. Examples of applications of such composition include elastic or stretchable bioelectronics, such as in the context of implantable medical devices, wearable electronic devices, and soft electronic devices; other biomedical devices; prosthetics; and other applications involving an interface with a human body, an animal body, or other biological tissue. Further and in view of its high electrical conductivity, such composition can be patterned to serve as stretchable conductors and can be included as interconnects or electrodes, such as neural recording/stimulation electrodes, or can be included in organic electronic devices, such as organic field effect transistors and organic light emitting diodes.

In some embodiments, the cross-linkable additive is a polyether monomer that includes a polyether moiety. In some embodiments, the polyether monomer includes a moiety —$(CH_2CH_2O)_x$—, where x is an integer that is 1 or greater than 1, such as 2 or greater, 3 or greater, 4 or greater, 5 or greater, 10 or greater, 15 or greater, and so forth. In some embodiments, the polyether monomer, alternatively or in conjunction, includes a moiety —$(CH_2O)_y$—, where y is an integer that is 1 or greater than 1, such as 2 or greater, 3 or greater, 4 or greater, 5 or greater, 10 or greater, 15 or greater, and so forth. More generally, in some embodiments, the polyether monomer includes one or more instances of a moiety -(A-O)—, where A is an alkylene group, such as containing 1 to 10, 1 to 8, 1 to 6, 1 to 4, or 1 to 2 carbon atoms. In some embodiments, the polyether monomer includes one or more crosslinkable functional groups. In some embodiments, the crosslinkable functional groups are end groups.

In some embodiments, the crosslinkable functional groups are acrylate groups. In some embodiments, the polyether monomer is a polyether diacrylate. In some embodiments, the crosslinkable functional groups are methacrylate groups. In some embodiments, the polyether monomer is a polyether dimethacrylate. In some embodiments, the crosslinkable functional groups are epoxide groups. In some embodiments, the polyether monomer is a polyether diepoxide. In some embodiments, the crosslinkable functional groups are azide groups. In some embodiments, the crosslinkable functional groups are thiol and alkene groups, which can react via a thiol-ene reaction. In some embodiments, the polyether monomer has a molecular weight in a range of about 500 to about 40,000 or greater, such as about 700 to about 40,000, about 1,000 to about 40,000, about 4,000 to about 40,000, about 10,000 to about 40,000, about 700 to about 30,000, about 1,000 to about 30,000, about 4,000 to about 30,000, about 10,000 to about 30,000, about 700 to about 20,000, about 1,000 to about 20,000, about 4,000 to about 20,000, or about 10,000 to about 20,000.

More generally, in some embodiments, the crosslinkable additive is a monomer that includes a moiety (e.g., a saturated moiety that is devoid of a carbon-carbon double bond and devoid of a carbon-carbon triple bond) and one or more crosslinkable functional groups bonded to the moiety, such as end groups. The moiety can include one or more functional groups, such as hydroxyl groups, zwitterion groups, sulfonate groups, carboxylate groups, and phosphate groups. In some embodiments, the crosslinkable functional groups are acrylate groups. In some embodiments, the crosslinkable functional groups are methacrylate groups. In some embodiments, the crosslinkable functional groups are epoxide groups. In some embodiments, the crosslinkable functional groups are azide groups. In some embodiments, the crosslinkable functional groups are thiol and alkene groups, which can react via a thiol-ene reaction.

In some embodiments, the crosslinkable additive is water soluble or has a good water solubility. In some embodiments, water solubility of an additive can be represented in terms of an upper threshold amount of the additive that can dissolve in water to form a substantially homogenous solution, expressed in terms of milligrams of the additive per 1 gram of water and measured at, for example, 25° C. and 1 atmosphere. Examples of suitable additives include those having a water solubility, measured at 25° C. and 1 atmosphere, of at least about 0.05 mg/(1 g of water), at least about 0.1 mg/(1 g of water), at least about 0.2 mg/(1 g of water), at least about 0.3 mg/(1 g of water), at least about 0.4 mg/(1 g of water), or at least about 0.5 mg/(1 g of water), and up to about 1 mg/(1 g of water) or greater. In some embodiments, the crosslinkable additive is a non-ionic monomer that is devoid of an electrical charge.

In some embodiments, the electrically conductive polymer is poly(3,4-ethylenedioxythiophene):poly(styrenesulfonate) or PEDOT:PSS. Another electrically conductive polymer can be used in place of, or in combination with PEDOT:PSS, such as those containing aromatic cyclic groups (e.g., poly(fluorene), polyphenylene, polypyrene, polyazulene, polynaphthalene, poly(pyrrole), polycarbazole, polyindole, polyazepine, polyaniline, poly(thiophene), poly (p-phenylene sulfide), and poly(p-phenylene vinylene)).

In some embodiments, the crosslinkable additive is included in the photo-curable composition in an amount of at least about 8%, in terms of dry mass ratio relative to a mass of the electrically conductive polymer, such as at least about 10%, at least about 12%, or at least about 15%, and up to about 80%, or up to about 70%.

In some embodiments, the photo-curable composition also includes a photoinitiator. An example of the photoinitiator is 2-hydroxy-1-[4-(2-hydroxyethoxy)phenyl]-2-methyl-1-propanone. In some embodiments, the photoinitiator is included in a non-zero amount of up to about 1 wt. % relative to a total weight of the photo-curable composition, such as up to about 0.5 wt. % or up to about 0.1 wt. %.

In some embodiments, the photo-curable composition also includes a solvent. In some embodiments, the solvent is water.

In some embodiments, a manufacturing method includes: applying the photo-curable composition over a substrate to form a film over the substrate; and selectively curing regions of the film to form a patterned film.

In some embodiments, the photo-curable composition is applied over the substrate by, for example, spin-coating, drop-casting, printing, or another coating or liquid deposition technique.

In some embodiments, selectively curing the film is performed by photolithography, including selectively exposing the regions of the film to light, and developing and removing unexposed regions of the film. In some embodiments, selectively exposing the regions of the film includes exposing to ultraviolet light. In some embodiments, the ultraviolet light has a wavelength of about 365 nm, which fits well with various i-line mask aligners. In some embodiments, developing the film is performed using a solvent, such as water. In some embodiments, selectively curing the film includes crosslinking the additive included in the photo-curable composition to form a cross-linked network within the film.

In some embodiments, the manufacturing method further includes exposing the patterned film to an alcohol. In some embodiments, the alcohol is an alkanol, such as containing 1 to 6, 1 to 4, or 1 to 2 carbon atoms. In some embodiments, the alkanol is methanol.

In some embodiments, an electrical conductivity of the patterned film is at least or greater than about 100 S/cm, at least about 200 S/cm, at least about 300 S/cm, at least about 400 S/cm, at least about 500 S/cm, at least about 800 S/cm, at least about 1,000 S/cm, at least about 1,300 S/cm, at least about 1,500 S/cm, or at least about 1,800 S/cm, and up to about 2,000 S/cm or greater, or up to about 2,300 S/cm or greater.

In some embodiments, a maximum tensile strain of the patterned film is at least or greater than about 10%, at least about 15%, at least about 20%, at least about 25%, at least about 30%, at least about 35%, at least about 40%, at least about 45%, or at least about 50%, and up to about 80% or greater, or up to about 100% or greater.

In some embodiments, a light transmittance of the patterned film at a wavelength of 550 nm is at least or greater than about 30%, at least about 40%, at least about 50%, at least about 60%, or at least about 70%, and up to about 80% or greater.

In some embodiments in which the electrically conductive polymer is PEDOT:PSS, a molar ratio of PSS and PEDOT in the patterned film (as characterized by an atomic ratio of sulfur (S) in PSS and PEDOT) is about 1.8 or less, about 1.7 or less, about 1.6 or less, about 1.5 or less, or about 1.4 or less, and down to about 1.3 or less.

Among other things, the present Applicant recognizes that small molecule additives in existing PEDOT:PSS, tend to leach out of a PEDOT:PSS film after $H_2O$ and MeOH treatment and thereby lose their function as plasticizers and de-dopants.

In some existing publications (Reactive and Functional Polymers 120, 66-73 (2017)), the required amounts of PEGDA to photopattern PEDOT are substantially higher (at least 10 times higher than the disclosed embodiments). Therefore, due to a very high concentration of PEGDA involved in the process, the final conductivity is 1-2 orders of magnitude lower than the disclosed PEDOT.

Additionally and arguably, although there have been several reports about the stretchability of PEDOT after blending with certain additives, e.g., ionic liquid (Science Advances 3, e1602076 (2017)) or PEG (ACS Applied Material Interfaces 7, 18415-18423 (2015)), none of these systems can maintain their stretchability after immersing in water or other solvents because a lack of crosslinked network.

The present Applicant has discovered that a cross-linked network from PEGDA, however, can continue to maintain the high conductivity and stretchability of PEDOT:PSS after rinsing in solvents. Furthermore, the present Applicant has discovered that cross-linked additives as plasticizers and de-dopants inside poly(3,4-ethylenedioxythiophene):poly(styrenesulfonate) (PEDOT:PSS) can provide prolonged enhancement for conductivity, stretchability, and stability in an aqueous environment when compared to small molecule counterparts.

According to some aspects embodiments herein disclose a highly conductive (>1000 S/cm), stretchable (>50% strain), and a photopatternable PEDOT. This unique combination of important characteristics allows its further applications in stretchable electronic devices (e.g., field effect transistors, light emitting diode, photovoltaic solar cells) and electrophysiological probes.

Applicant has further has discovered that PEGDA serves as dual roles in enabling the high conductivity and stretchability. First of all, the PEG backbone is a softer chain compared to the rigid conjugated polymer. Therefore, the incorporation of PEGDA is an effective plasticizer that created more free volumes in the PEDOT system, and correspondingly higher stretchability. On the other hand, the highly polar nature of the PEG backbone can serve as a competitive dopant for PEDOT. By inserting into the original PEDOT-PSS domain, PSS would be effectively swept by the newly bounded PEGDA, and it would leave the spin coated PEDOT film with better packing and less insulating PSS for higher conductivity.

In the embodiments disclosed, the concentration range of PEGDA may vary mostly depending on the substrate surface energy. With a more sticky surface such as SEBS, the amount of PEGDA would be lower, e.g., 5-10 mg PEGDA per 1 mL of PEDOT. If the surface energy of the substrate is lower, such as PU, the amount of PEGDA can be higher, e.g., 5-25 mg PEGDA per 1 mL of PEDOT. The lower bound of PEGDA is to have enough crosslinker to form a dense film for photopatterning. The upper bound of PEGDA is to avoid too much physical crosslinking of the PEDOT film that cannot be developed after photopatterning.

Those skilled in the art may appreciate that the molecular weight of PEGDA depends on two factors. The lower bound is determined by its water solubility. When the MW is lower than 700, PEGDA can no longer be mixed well with water, leading to significant phase separation during spin coating. The upper bound of PEGDA depends on its crystallinity. When the MW is higher than 20,000, PEGDA would form large crystals after spin coating, leading to low stretchability. Therefore, embodiments described are based on results of testing PEGDA with MW between 700 and 20,000.

Applicant has discovered that with respect to the additives that, in order to use a polymeric additive that can work with PEDOT, there are several important considerations given the physicochemical characteristic of the PEDOT:PSS system. First of all, commercial PEDOT:PSS is in a water dispersion, which requires a good water solubility of the additive. To this end, only polymer with polar or even ionic backbones can be used. However, since PEDOT:PSS is also a colloidal suspension stabilized by the surface charges and solution pH, ionic polymer would inevitably disrupt the surface charges of PEDOT:PSS, leading to physical coagulation. In light of these two facts, only non-ionic polar polymers can be considered. Among all the possible candidates, PEG-DA is the most reasonable and promising one. Besides the bifunctionalized PEG-DA, multi-arm branched PEG acrylates can also be used to yield stretchable, conductive, and photopatternable PEDOT.

In addition to PEG-based macromonomers, other small molecular monomers while using PEGDA only as the crosslinker can also be used. These small molecular monomers include acrylic acid, hydroxylethyl methacrylate, and zwitterionic methacrylates.

It should be noted that the disclosed embodiments are a result of experimentation using (meth)acrylate-based free radical chemistry because of its high reactivity and selectivity to avoid random attacks of PSS, which would lead to poor conductivity and stretchability. Nevertheless, other crosslinking chemistry can also be used to photopattern PEDOT, such as water soluble bisazide or bisbenzophenone.

Applicant has further discovered that, if the additives (in the form of monomers) can be photo-cross-linked, they can further allow for direct photo-patterning of PEDOT:PSS. An example of this is shown in FIG. 1.

FIG. 1 is a diagram illustrating an existing type of PEDOT:PSS polymer structure and a PEDOT:PSS polymer structure with a cross-linked network which can allow for direct photo patterning, according an embodiment of the present disclosure.

As shown FIG. 1 includes a PEDOT:PSS 100 in a non-aqueous environment and a monomer 102, a PEDOT:PSS polymer 104 in an aqueous environment with some additives, and a cross-linked network 106 made of a plurality of monomers 102. By way of comparison it can be seen the molecules of 104 PEDOT:PSS can provide prolonged enhancement for conductivity, stretchability, and stability in an aqueous environment compared to the molecules PEDOT:PSS. The inclusion of the cross-linked network 104 made of monomers, can allow for direct photo-patterning of PEDOT:PSS.

The present Applicant has further discovered that compared to diacetylene-based photo-patterning, the use of PEGDA allows photo-patterning to be performed with about 365 nm ultraviolet (UV) light, instead of about 254 nm light, which fits well with various i-line mask aligners. Additionally, the PEGDA photo-crosslinking reaction has less restriction son monomer configuration, whereas diacetylene has to be well aligned to form a ladder-type polymer. Additionally, the present Applicant has discovered that for direct photo patterning PEDOT:PSS, in a typical preparation, PEDOT:PSS can be mixed with poly(ethylene glycol) diacrylate (PEGDA) macromonomers and a resulting mixture can be photo-cured after spin-coating onto a stretchable substrate to form a film. Later, the film can be treated with water ($H_2O$) and methanol (MeOH) to develop patterns and improve the crystallinity of PEDOT. Testing of the conductivity can be performed using a four-probe method with Keithley, testing of the stretchability can be performed using a stretching station, and testing of the electrochemical impedance can be performed using a Biologic potentiostat.

The following experimental protocols have been followed for embodiments of the present disclosure. For preparation of a stretchable substrate, a hydrogenated styrene butadiene block copolymer (SEBS|H1062) is used as an example. SEBS is dissolved into cyclohexane at a concentration of about 100 mg/mL under about 70° C. A resulting solution is drop-casted onto a glass slide with a size of about 1 inch by about 1 inch and left overnight. For a PEDOT:PSS solution, a stock solution (PH1000) is freshly filtered through a 1 μm nylon syringe filter and weighed to about 1 g in a 20 mL glass vial. About 5 mg of PEGDA (of various molecular weights (MW)) is weighted, and added along with about 0.5 mg of a photoinitiator (2-hydroxy-1-[4-(2-hydroxyethoxy) phenyl]-2-methyl-1-propanone 112959) into the glass vial and vortexed to mix well. A resulting mixture is spin-coated on $O_2$ plasma-treated SEBS at about 2000 rpm for about 30 s and a resulting film is vacuum dried for about 1 min at room temperature. The film is cured using an UV lamp at sub-basement for about 1-5 min with a shadow mask atop to pattern an electrode array. Patterns are developed using $H_2O$ and the patterned film is treated for about 10 min using MeOH. The patterned and treated film is vacuum dried after the MeOH treatment and conductivity, stretchability, and impedance tests are then performed.

Some embodiments of directly photo-patternable, conductive and stretchable PEDOT:PSS and experimental data associated with those as set forth above will now be described below.

It has been discovered by the present Applicant that PEGDA allows direct photo-patterning of PEDOT:PSS or in other words, with the incorporation of the PEGDA additive, direct photo-patterning of PEDOT:PSS can be achieved. It is noticed that a sharp pattern contrast can be achieved within a specific concentration window of PEGDA and PEDOT. The concentration window is dependent on both substrate selection and PEDOT:PSS formulation.

Figure 2:
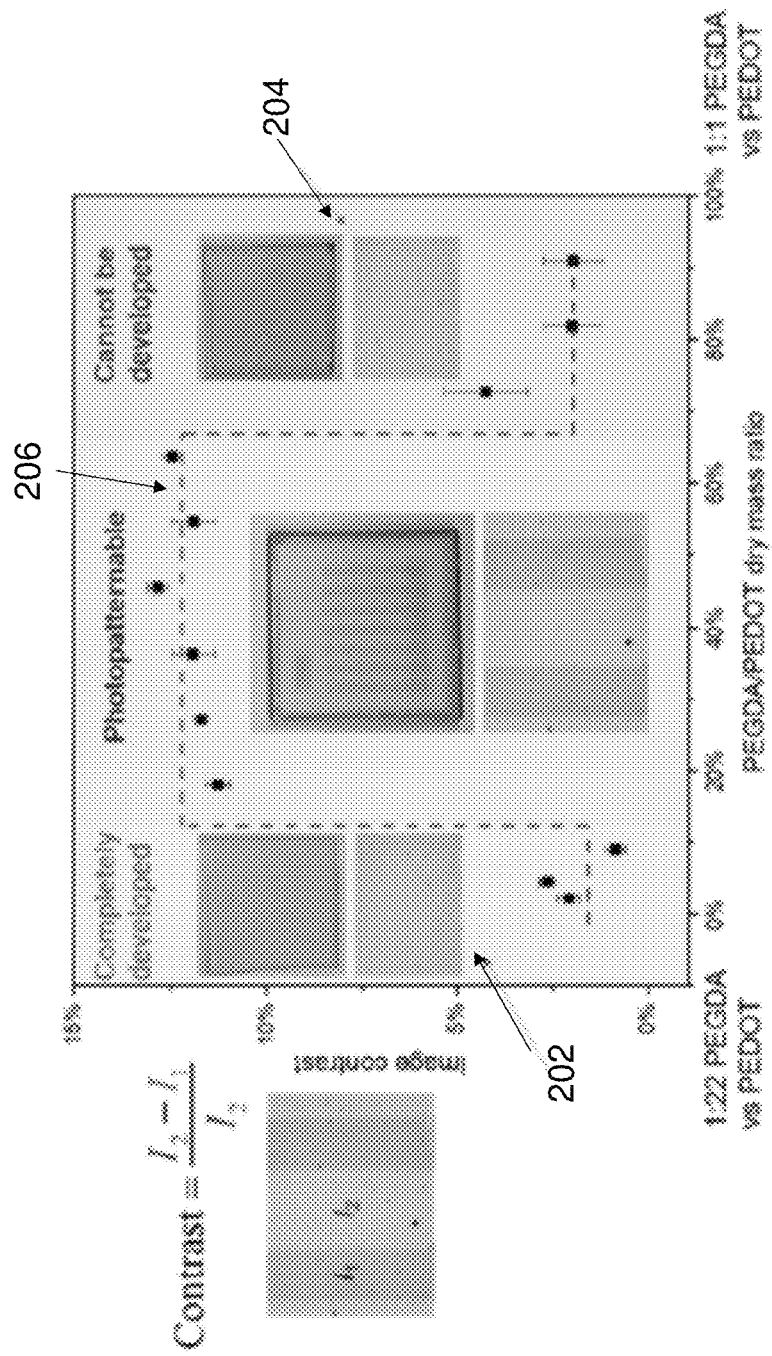
FIG. 2 provides a graph of various poly(ethylene glycol) diacrylate (PEGDA) vs. PEDOT concentrations, according an embodiment of the present disclosure.

An example of this is shown in FIG. 2 which provides results on SEBS (H1062) from an example demonstration.

More specifically, FIG. 2 provides a graph of various PEGDA vs. PEDOT concentrations. As can be seen the x-axis shows PEGDA vs. PEDOT dry mass ratio ranging from 0% to 100%. The 0% may correspond to PEGDA vs. PEDOT ratio of 1:22. The 100% may correspond to PEGDA vs. PEDOT ratio of 1:1. The y-axis shows image contrast ranging from 0% to 15%. For this example, the contrast may be given by:

$$\text{Contrast}=(I_2-I_1)/I_2 \quad (1)$$

where $I_1$ is the image intensity of the crosslinked area and $I_2$ is the image intensity of the non-crosslinked area. As shown in the region 202 (from 0% to approximately 12% of the PEGDA/PEDOT dry mass ratio), the PEDOT:PSS structure 100 is completely developed and therefore, there may not be enough monomers to form a cross-linked network and therefore photo patterning may not be possible. In the region 204 (from approximately 65% to 100% of PEGDA/PEDOT dry mass ratio), the PEDOT:PSS structure 100 cannot be developed due to the good film integrity originated from the high viscosity. Other additives that will gel PEDOT cannot be patterned either. In the region 206 (from approximately 12% to 65% of the PEGDA/PEDOT dry mass ratio) the PEDOT:PSS structure 100 is photopatternable. The region 206 may therefore be considered as the concentration window.

Figure 3:
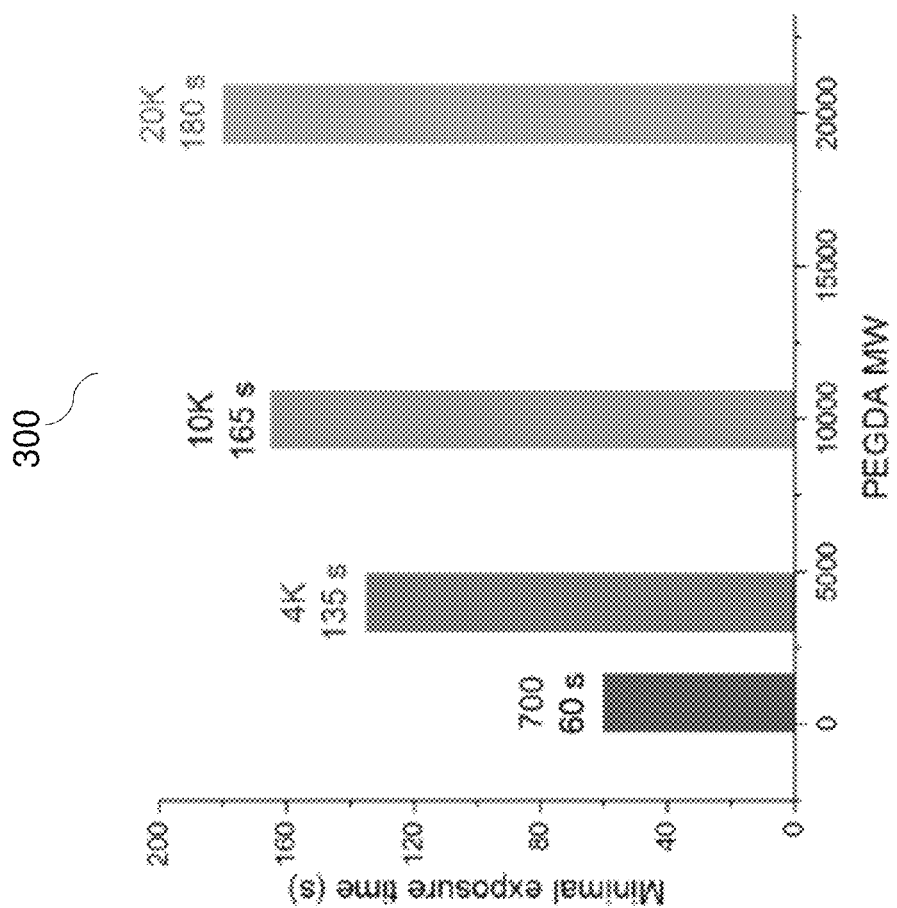
FIG. 3 is a diagram illustrating a graph 300 of molecular weight of PEGDA in molecular weight (MW) vs. minimum exposure time in seconds, according an embodiment of the present disclosure.

FIG. 3 is a diagram illustrating a graph 300 of molecular weight of PEGDA in MW on x-axis versus minimum exposure time in seconds on y-axis. The graph 300 illustrates example experimental results in which a mass of 5 mg PEGDA was added to 1 ml of PEDOT solution. It may be appreciated from the graph that when the total mass of the PEGDA additive is fixed, a minimal exposure time for patterning is inversely related to the MW of PEGDA. In other words, when the same mass of additive is added, smaller MW PEGDA requires shorter exposure time to be patterned.

Figure 4:
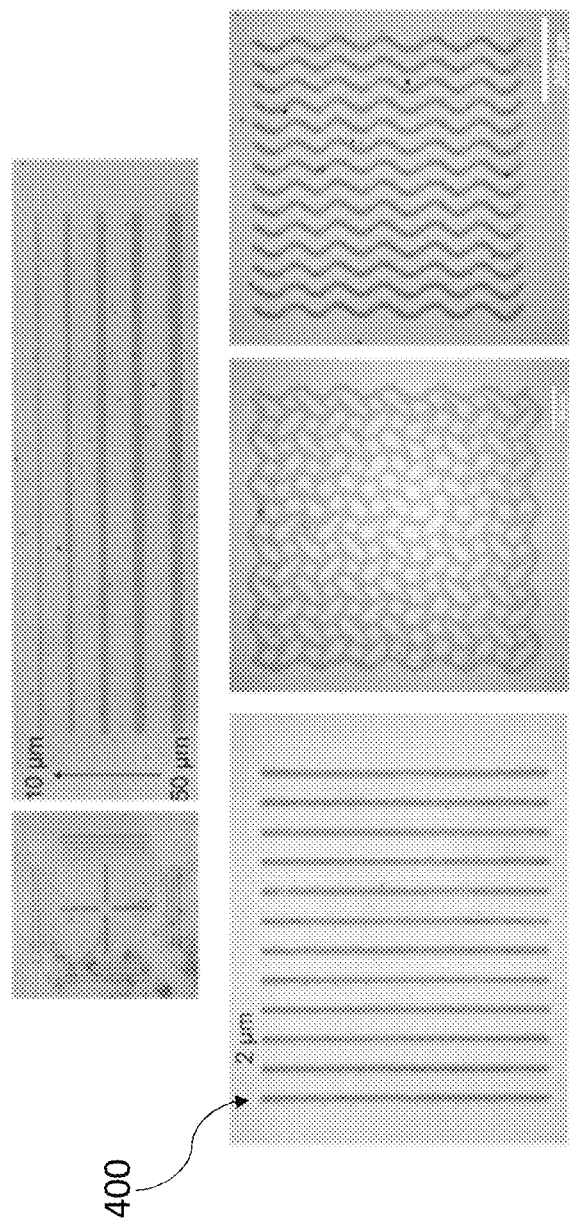
FIG. 4 is a diagram illustrating a minimal possible feature size for photo patterning of PEDOT, according to an embodiment of the present disclosure, according an embodiment of the present disclosure.

FIG. 4 is a diagram illustrating a minimal feature size that can be achieved with photo patterning of PEDOT, according to an embodiment of the present disclosure.

A shown by 400, a minimal feature size of about 2 μm can be achieved with photo-patterning.

Figure 5:
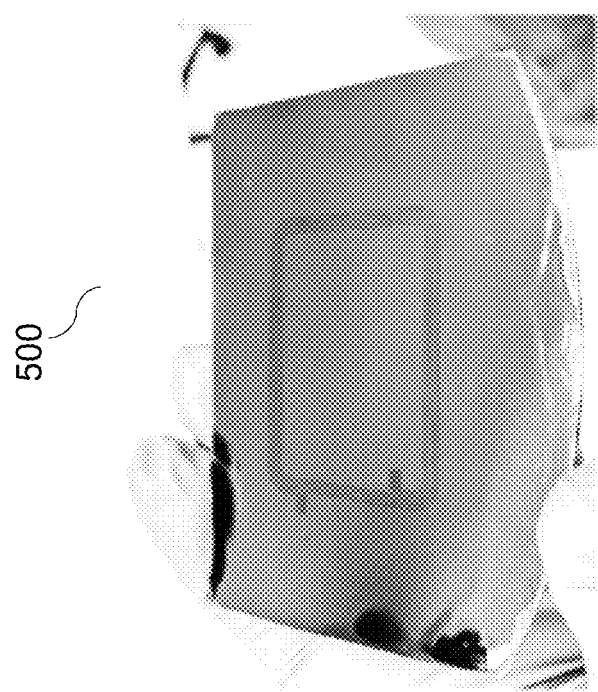
FIG. 5 is a diagram illustrating an example large-scale device which can be photo patterned, according to an embodiment of the present disclosure, according an embodiment of the present disclosure.

FIG. 5 is a diagram illustrating an example large-scale device 500 which can be photo patterned, according to an embodiment of the present disclosure. The large-scale device shown is an antenna with an approximate dimensions of 7.5 cm in length and 5 cm in width. There can be other large scale devices which may be photopatterned with methods disclosed herein.

It has also been discovered by the applicant that a cross-linked PEGDA can sustain MeOH treatment to boost PEDOT conductivity. After a photo-patterning process, a PEGDA-supplemented film can survive a subsequent MeOH treatment because a cross-linked network can stay intact.

Figure 6:
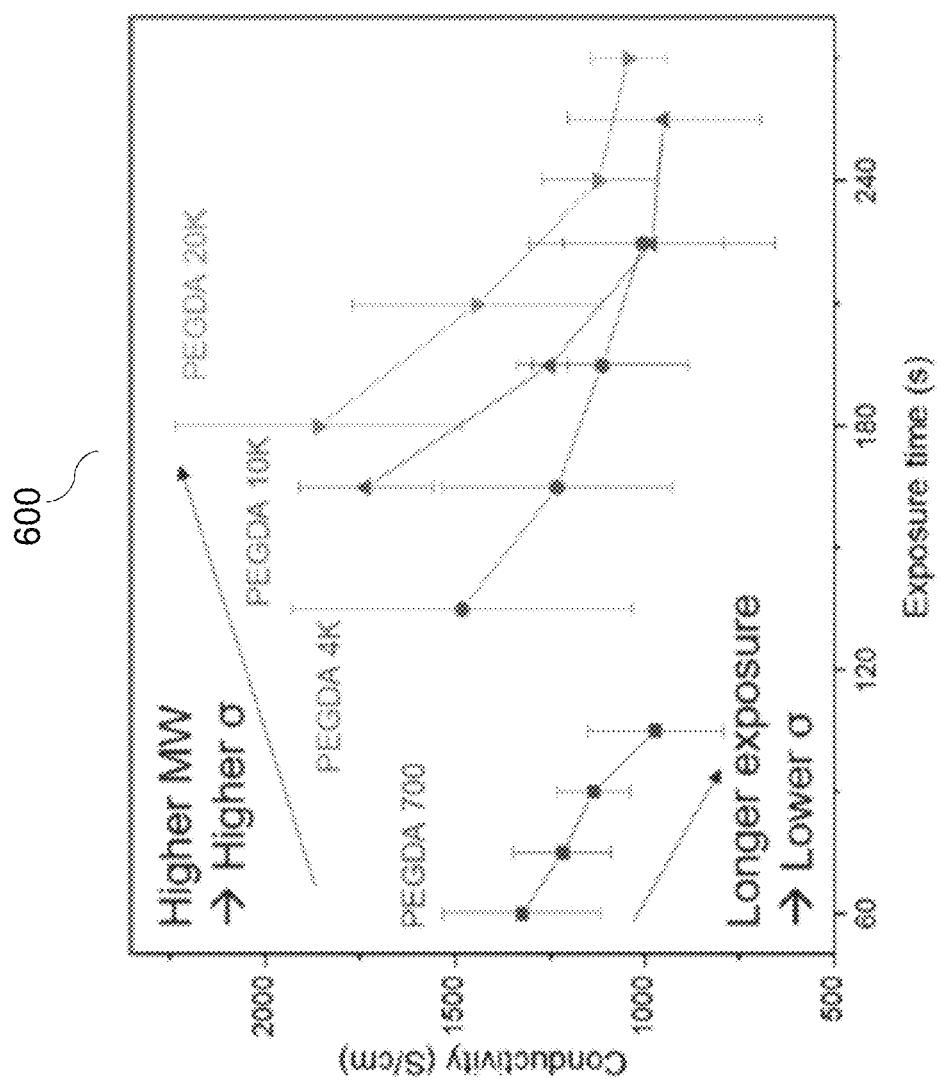
FIG. 6 is a diagram illustrating a graph 600 of conductivity of a PEGDA-supplemented PEDOT:PSS film after MeOH treatment, according an embodiment of the present disclosure.

FIG. 6 is a diagram illustrating a graph 600 of conductivity of a PEGDA-supplemented PEDOT:PSS film after MeOH treatment. The graph 600 shows an exposure time in seconds on x-axis and conductivity in S/cm on y-axis for various PEDOT films having various amounts of PEGDA in MW particularly PEGDA 700, PEGDA 4K, PEGDA 10K, and PEGDA 20K. As can be understood from the graph by those skilled in the art, after the treatment, all tested PEDOT films showed consistently high conductivities (>about 1000 S/cm) although shorter exposure time and larger MW of PEGDA can yield slightly higher values.

Additionally, it has been discovered by the Applicant that PEGDA helps with the PSS removal as a dedopant. In other words, the addition of PEGDA can already remove a substantial amount of PSS. More specifically, X-ray photoelectron spectroscopy (XPS) characterizations showed that the incorporation of PEGDA can facilitate the removal of PSS, and the subsequent MEOH treatment can further reduce the PSS content in the resulting treated film. An example result of such an experiment is shown in FIG. 7.

Figure 7:
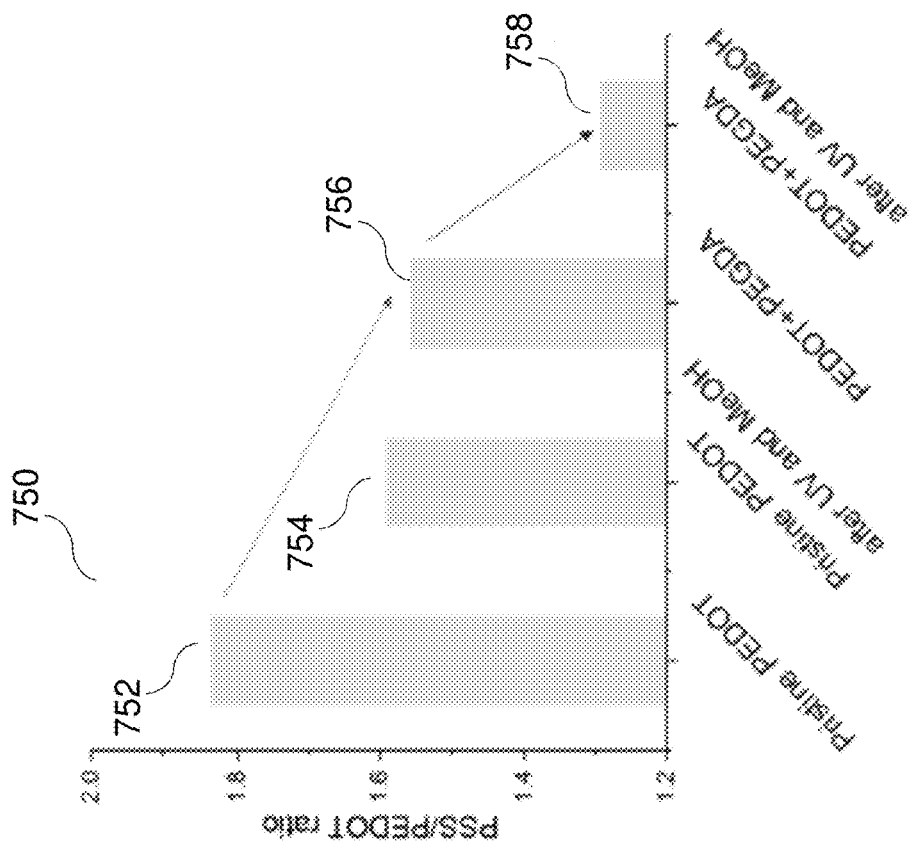
FIG. 7 provides graphs of example experimental results of X-ray photoelectron spectroscopy (XPS), according an embodiment of the present disclosure.
Figure 7:
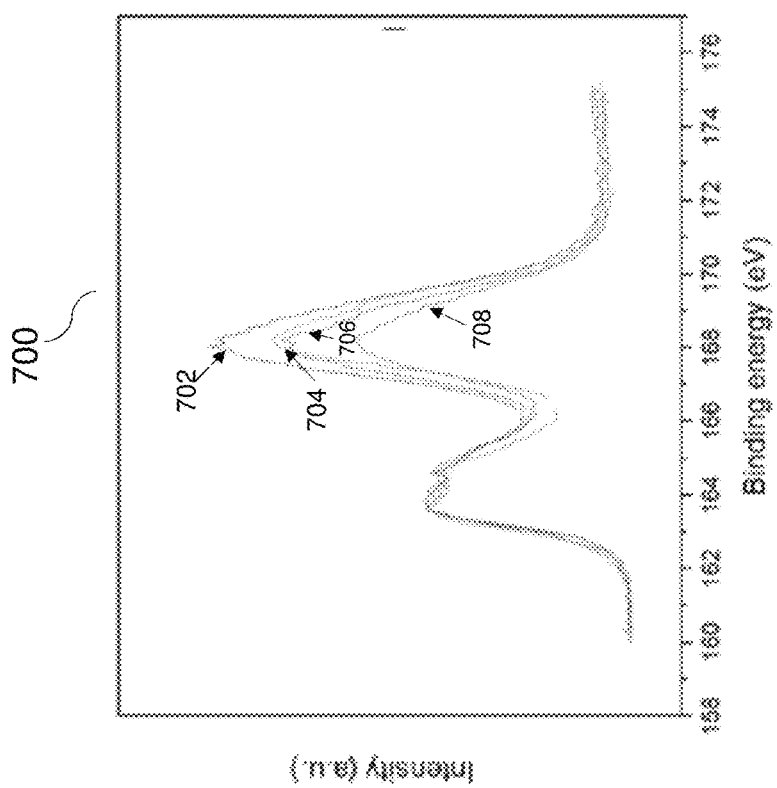

FIG. 7 provides graphs 700 and 750 illustrating experimental results of X-ray photoelectron spectroscopy (XPS). The graph 700 shows intensity in (a.u.) on y-axis and binding energy in eV on x-axis. Furthermore, the graph 700 shows curves 702 for a pristine PEDOT, 704 for PEDOT plus PEGDA, 706 for pristine PEDOT after UV and MeOH, and 708 for PEDOT plus PEGDA after UV and MeOH. As can be seen the intensity for the curve 704 (PEDOT+PEGDA) is lower than the intensity for the curve 702 (pristine PEDOT), indicating that addition of PEGDA can reduce the PSS. Similarly, the intensity for the curve 708 (PEDOT+PEGDA after UV and MeOH) is lower than the intensity for the curve 706 (pristine PEDOT after UV and MeOH), indicating that addition of PEGDA can reduce the PSS.

The graph 750 shows PSS/PEDOT ratio on y-axis for various PEDOTs on x-axis including pristine PEDOT 752, pristine PEDOT after UV and MeOH 754, PEDOT+PEGDA 756, and PEDOT+PEGDA after UV and MeOH 758. As can be seen the PSS/PEDOT ratio is the highest in 752, it is slightly lower in 754, even lower in 756, and the lowest in 758. As such it can be easily understood that the PEDOT can help with PSS removal. There can be further improvement in PSS removal by the use of MeOH as indicated by 758.

Applicant has further discovered from experimental X-ray diffraction that PEGDA first causes the disruption of π-π packing of PEDOT.

Figure 8:
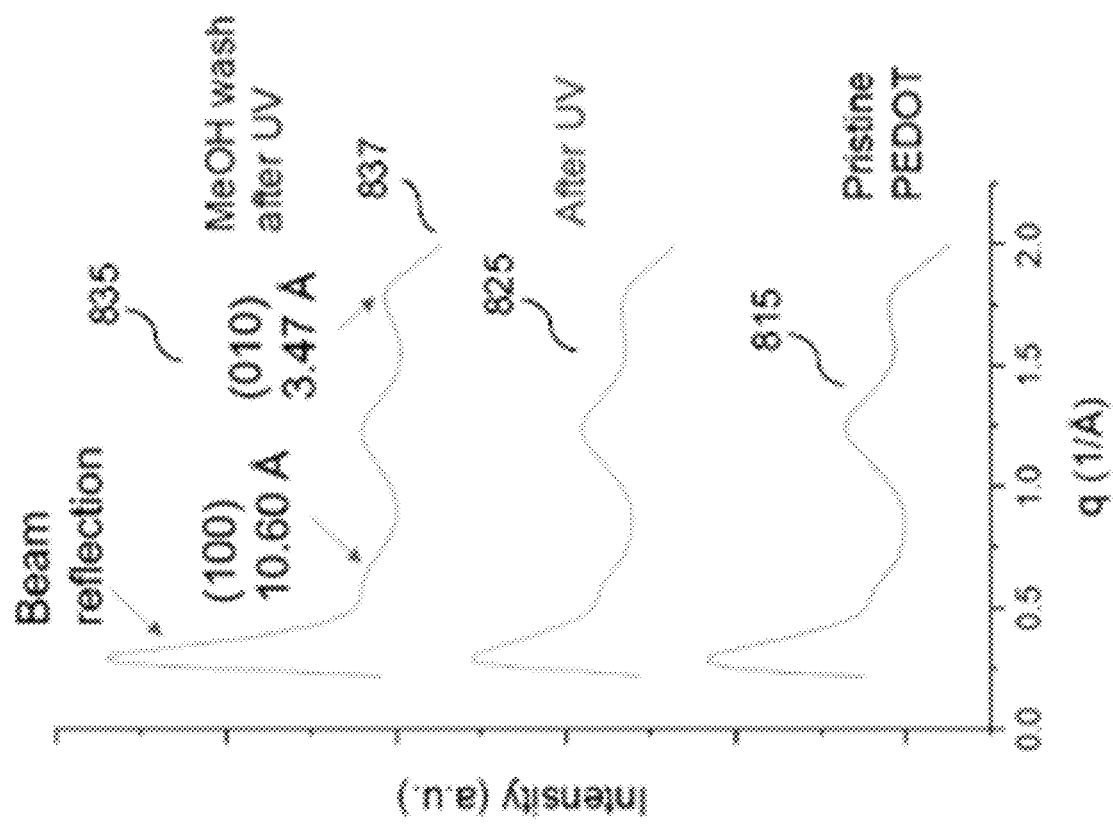
FIG. 8 provides example experimental results and graphs of X-ray diffractions for various PEDOT films, according an embodiment of the present disclosure.

FIG. 8 provides results of an X-ray diffraction for a pristine PEDOT, pristine PEDOT after UV, and pristine PEDOT after UV with MeOH wash; and corresponding graphs 815, 825, 835 respectively. The graphs 815, 825, and 835 show q (1/A) on x-axis and intensity in astronomical unit (a.u.) on y-axis. In the graph 835 illustrates a peak (010) having an x-axis value 3.47 Å as indicated by 837 which is a manifestation of a pi-pi (π-π) stacking. The (010) peak is well resolved.

Applicant has further discovered that the π-π packing of PEDOT is later restored through the MeOH treatment. An example of this is shown in FIG. 9.

Figure 9:
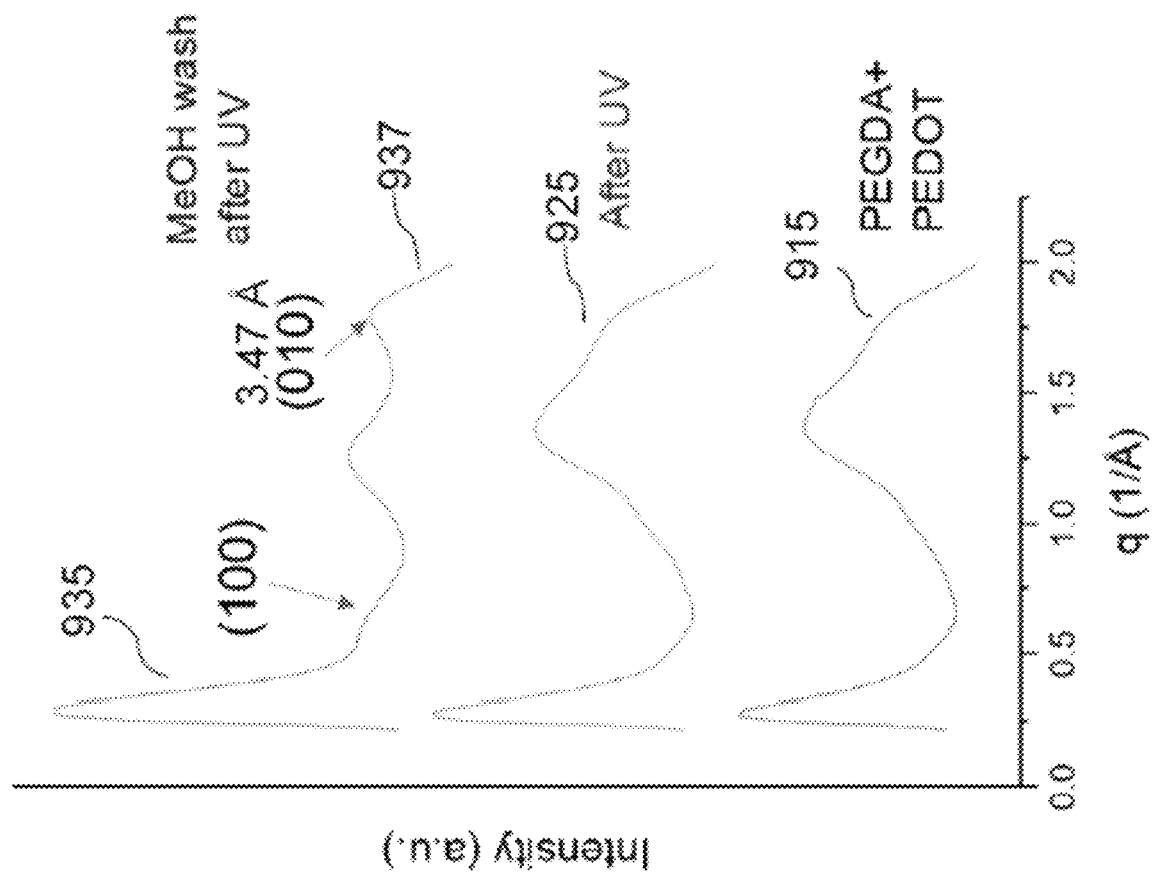
FIG. 9 provides example experimental results and graphs of X-ray diffractions for various PEGDA supplemented PEDOT film, according an embodiment of the present disclosure.

FIG. 9 provides results of an X-ray diffraction for a PEDOT+PEGDA, PEDOT+PEGDA after UV, and PEDOT+PEGDA after UV with MeOH wash; and corresponding graphs 915, 925, 935 respectively. The graphs 915, 925, and 935 show q (1/A) on x-axis and intensity in astronomical unit (a.u.) on y-axis. The graph 935 also shows the (010) peak 937 with the x-axis value of 3.47 Å. However, as can be seen, by a simple visual comparison, the same peak (010) in FIG. 9 is just a small shoulder peak indicating a weak distribution. In other words, if relative intensity values shown on y-axis are compared for both FIG. 8 and FIG. 9, then it may be observed that the peak intensity of 937 is lower than the peak intensity of 837 indicating a disordered pi-pi stacking.

It has been further discovered by the Applicant that PEGDA-supplemented PEDOT:PSS film exhibits good stretchability after MeOH treatment. An example of this is shown in FIG. 10.

Figure 10:
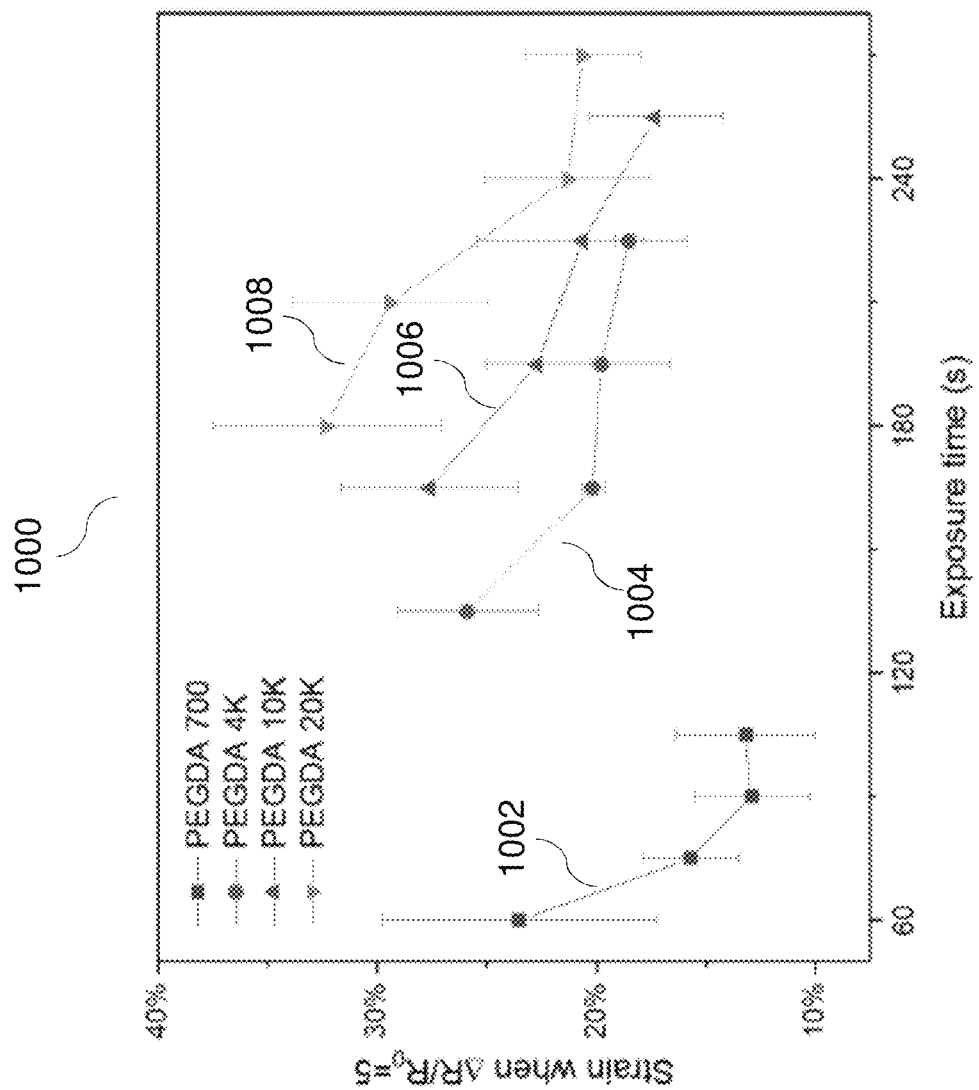
FIG. 10 provides a graph 1000 of strain vs. exposure time for various cross-linked PEGDA films, according an embodiment of the present disclosure.

FIG. 10 provides a graph 1000 of strain vs. exposure time for cross-linked PEGDA films. The graph 1000 shows exposure time in seconds on x-axis and strain on y-axis. Further the graph 1000 shows a curve 1002 for PEGDA 700, a curve 1004 for PEGDA 4K, a curve 1006 for PEGDA 10K, and a curve 1008 for PEGDA 20K. As can be seen, the as the MW increases from 700 to 20K, the strain range also increases from approximately (12%-24%) to approximately (22%-33%).

After MeOH treatment, cross-linked PEGDA films showed good stretchability. This aspect can be further improved with tuning of PEDOT:PSS formulation and substrate design Similar to the conductivity data, longer exposure time and smaller MW of PEGDA tend to yield lower stretchability, presumably due to a higher crosslinking density.

Figure 11:
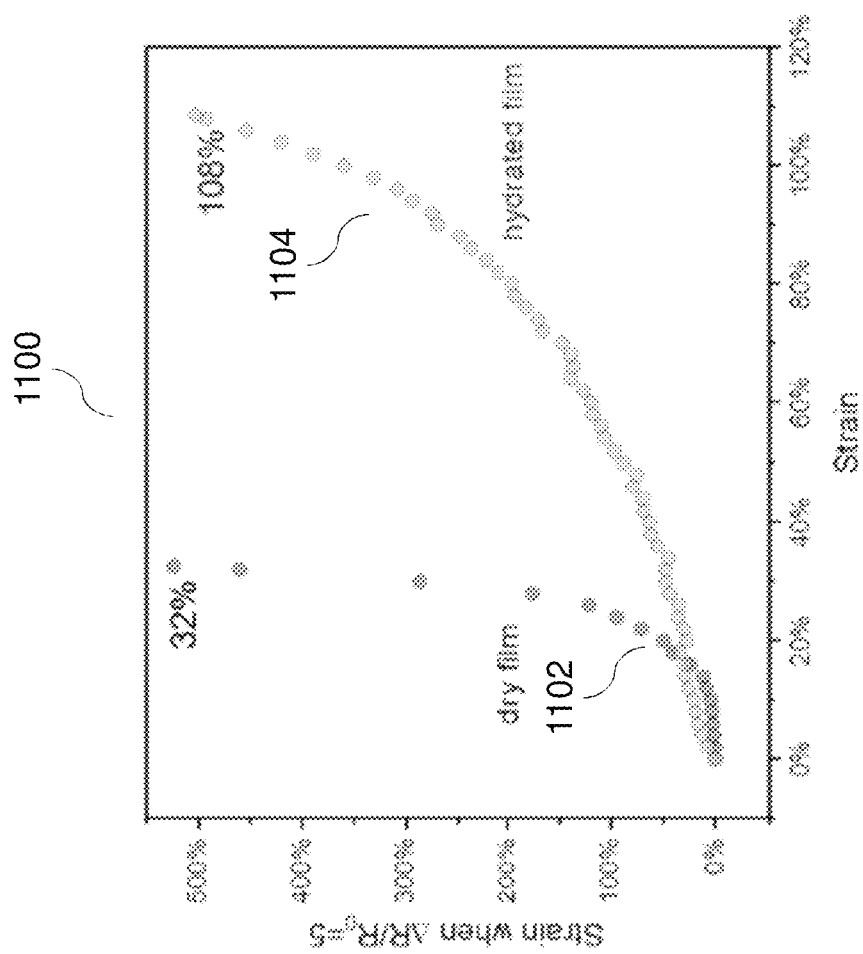
FIG. 11 is a graph 1100 of stretchability of a dry PEGDA supplemented PEDOT:PSS film and a hydrated PEGDA supplemented PEDOT:PSS film, according an embodiment of the present disclosure.

FIG. 11 is a graph 1100 illustrating a comparison of experimental results of stretchability of a dry PEGDA supplemented PEDOT:PSS (PEDOT+PEGDA) film 1102 and a hydrated PEDOT+PEGDA film 1104. As can be seen, when immersed in water, the stretchability is boosted, up to about 3-fold Swelling of a cross-linked PEGDA network provides an enhanced stretchability in an underwater environment.

It has also been discovered by the Applicant that PEGDA-supplemented PEDOT:PSS film exhibits superior properties such as a lower impedance and a larger charge storage capacity versus ionic liquid-treated PEDOT:PSS. Furthermore, an example of these is shown in FIG. 12 and FIG. 13.

Figure 12:
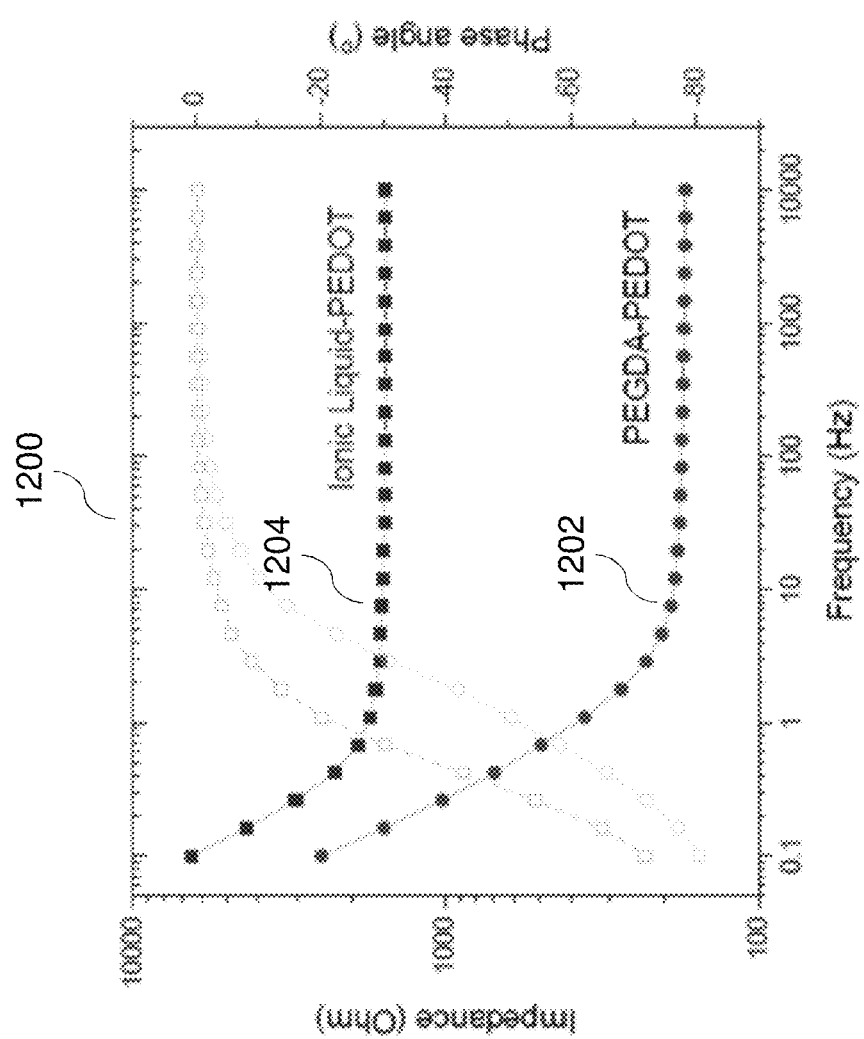
FIG. 12 is a graph 1200 of impedance vs. frequency of a PEGDA supplemented PEDOT:PSS film and an ionic liquid treated PEDOT:PSS film, according an embodiment of the present disclosure.

FIG. 12 is a graph 1200 illustrating impedance versus frequency of a PEGDA supplemented PEDOT:PSS film 1202 versus ionic liquid treated PEDOT:PSS film 1204. As can be seen, the PEGDA-supplemented PEDOT:PSS film 1202 exhibits a lower impedance as compared to the ionic liquid-treated PEDOT:PSS film 1204.

Figure 13:
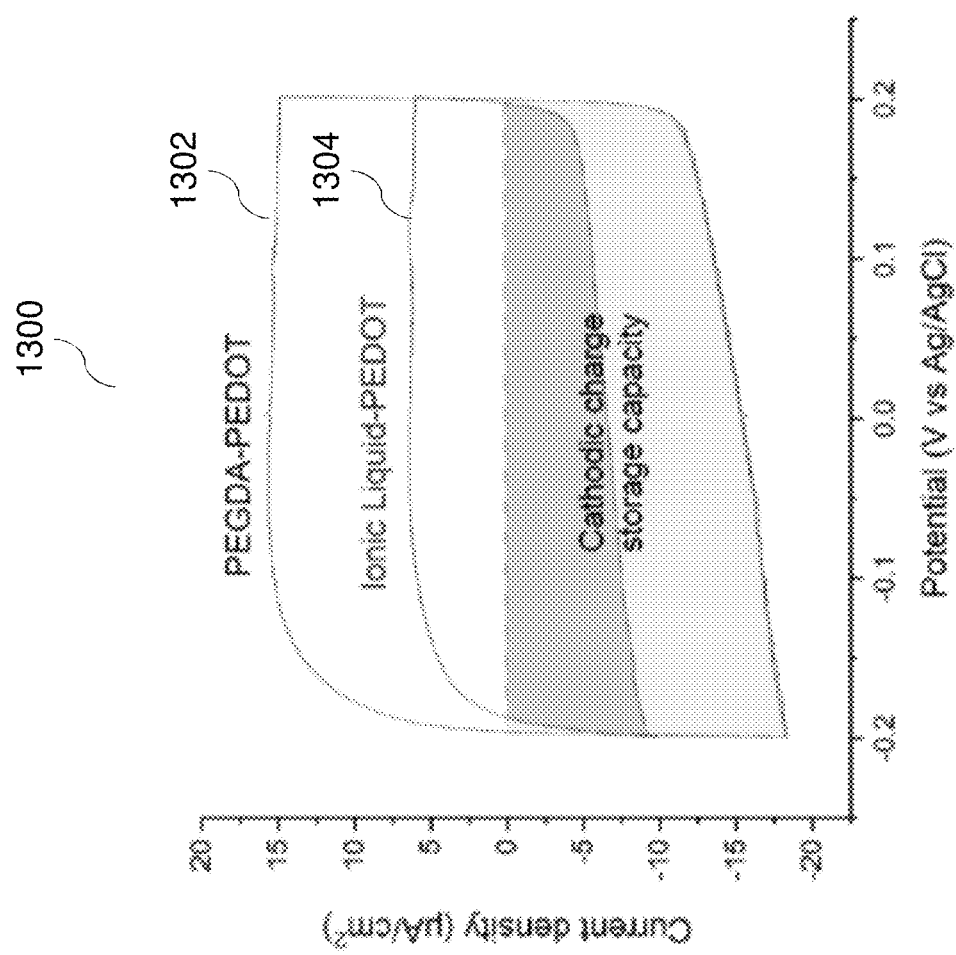
FIG. 13 is a graph 1300 of current density vs. potential of a PEGDA supplemented PEDOT:PSS film and ionic liquid treated PEDOT:PSS film 1304, according an embodiment of the present disclosure.

FIG. 13 is a graph 1300 illustrating current density versus potential of a PEGDA supplemented PEDOT:PSS film 1302 versus ionic liquid treated PEDOT:PSS film 1304. As can be seen, the PEGDA-PEDOT film 1302 exhibits a current density of approximately 15 µA, whereas the ionic liquid PEDOT film 1304 exhibits a current density of approximately 5 µA. As can be seen, the PEGDA-supplemented PEDOT:PSS film 1302 exhibits a larger charge storage capacity as compared to the ionic liquid-treated PEDOT:PSS film 1304.

As stated before, the present Applicant has discovered that after the MeOH treatment, the crosslinked PEGDA films show good stretchability. In one example, compared to a pure PEDOT film, the PEGDA-PEDOT film can be stretched to ~50% without cracks. Some experimental data regarding this aspect is further shown in FIGS. 14 and 15.

Figure 14:
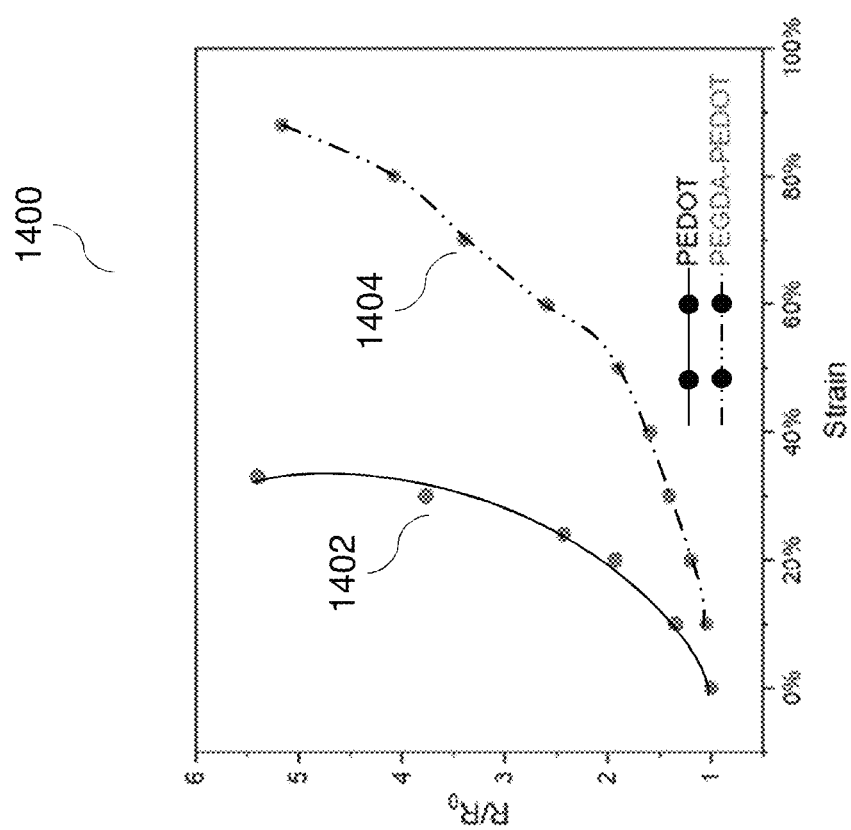
FIG. 14 is a graph 1400 of stretchability of a pure PEDOT film and a PEGDA-PEDOT film according an embodiment of the present disclosure.

FIG. 14 is a graph 1400 showing stretchability of a pure PEDOT film and a PEGDA-PEDOT film according an embodiment of the present disclosure. The graph 1400 shows strain on x-axis and normalized resistance change on y-axis. The graph 1400 includes a curve 1402 for a pure PEDOT film and a curve 1404 for a PEGDA-PEDOT film according to one aspect. As can be see the PEGDA-PEDOT film exhibits a higher percentage of strain compared to the pure PEDOT film. In other words, the PEGDA allows a significantly enhanced stretchability of PEDOT.

Figure 15:
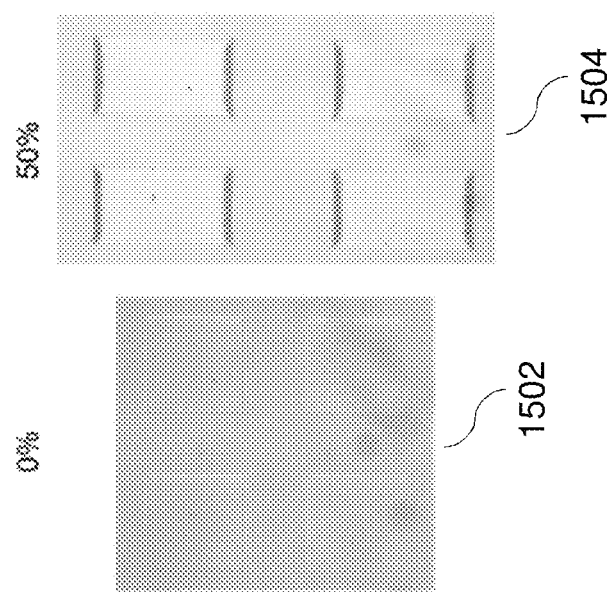
FIG. 15 shows example images of a photopatterned PEGDA-PEDOT before and after stretching, according an embodiment of the present disclosure.

FIG. 15 shows example images of a photopatterned PEGDA-PEDOT film before and after stretching. The image 1502 is before stretching and image 1504 is after stretching by approximately 50%. As can be seen that the stretched film 1504 does not have any cracks.

Applicant has further discovered that when coated on gold (Au) films, PEGDA-PEDOT can substantially reduce the total impedance and improve the charge storage capacity (CSC) of Au. Both the interfacial capacitance and CSC are linearly proportional to the volume of the PEDOT. Experimental data related to these aspects is shown in FIGS. 16 and 17.

Figure 16:
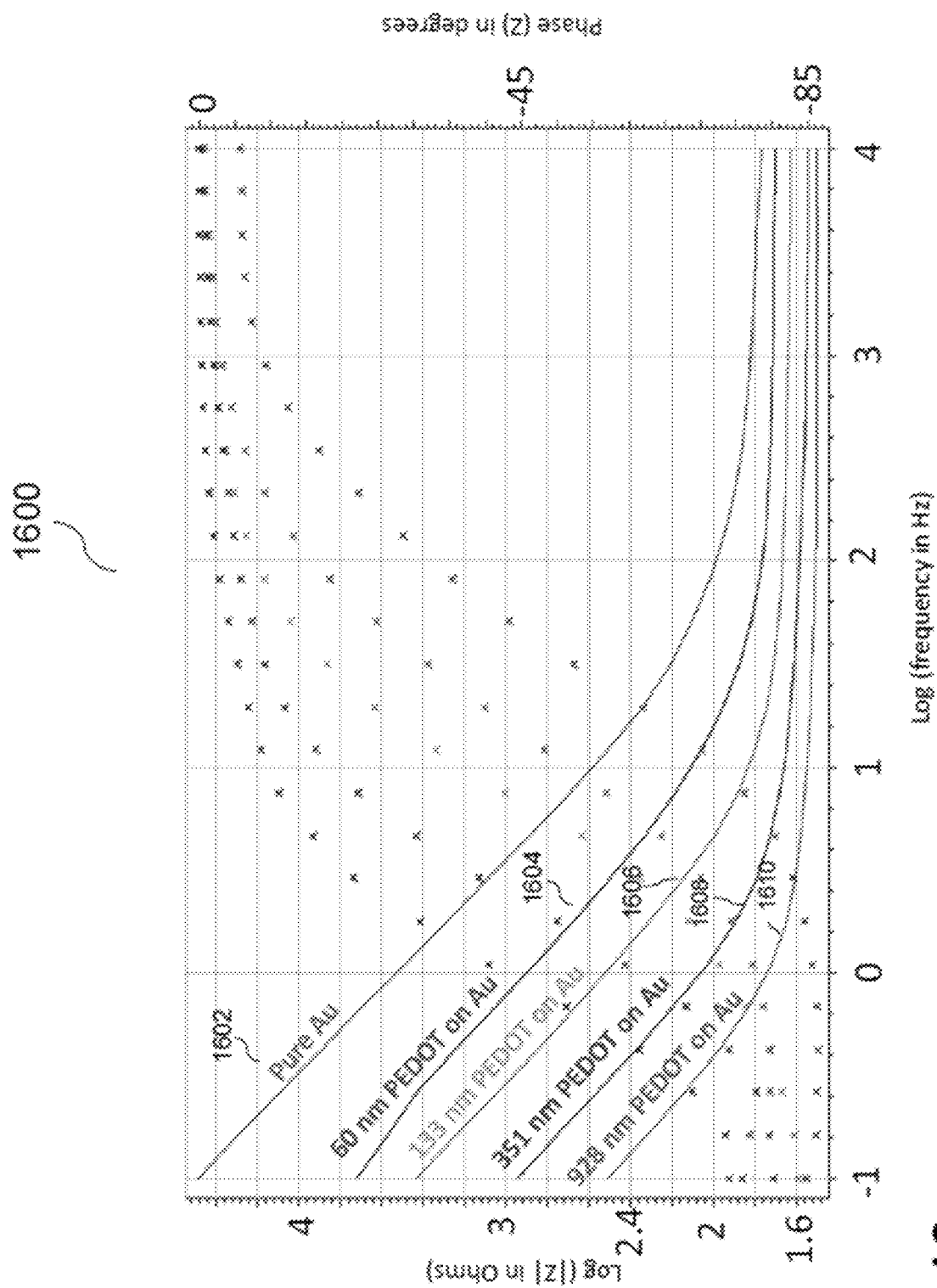
FIG. 16 is a graph 1600 of impedance versus frequency of gold (Au) films coated with various thicknesses of PEGDA-PEDOT, according an embodiment of the present disclosure.

FIG. 16 is a graph 1600 of impedance versus frequency of gold (Au) films coated with various thicknesses of PEGDA-PEDOT based on electrochemical impedance spectroscopy (EIS) data. The graph 1600 shows frequency (Hz) in logarithmic scale on the x-axis and impedance (Ohms) in logarithmic scale on the y-axis. The graph 1600 includes a curve 1602 for a pure Au film, a curve 1604 for an Au film with 60 nm PEGDA-PEDOT coating, a curve 1606 for an Au film with 133 nm PEGDA-PEDOT coating, a curve 1608 for an Au film with 351 nm PEGDA-PEDOT coating, and a curve 1610 for an Au film with 928 nm PEGDA-PEDOT coating. As can be seen, for higher amounts of PEGDA-PEDOT coating, the impedance of the Au film decreases.

Figure 17:
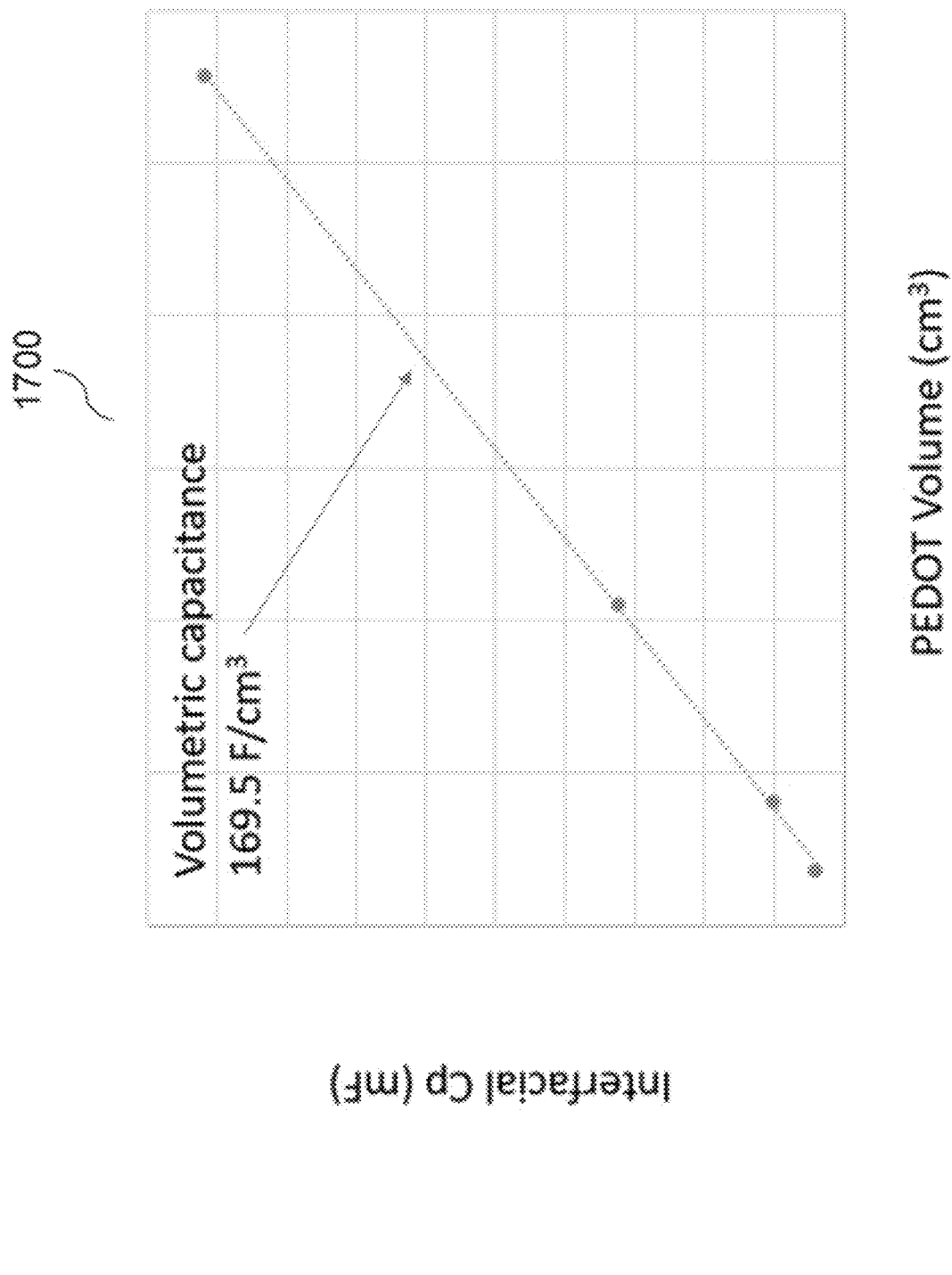
FIG. 17 is a graph 1700 of volumetric capacitance of a PEGDA-PEDOT film, according an embodiment of the present disclosure.

FIG. 17 is a graph 1700 of volumetric capacitance of the PEGDA-PEDOT coated Au film referred to in FIG. 16. The volumetric capacitance shown is fitted from the EIS data and is equal to 169.5 F/cm$^3$ in one example. The graph 1700 shows PEDOT volume in cm$^3$ on the x-axis and interfacial capacitance in mF on y-axis. As can be seen, the interfacial capacitance of the PEGDA-PEDOT coated Au film is linearly proportional to the volume of the PEDOT. More particularly, in one example, the interfacial capacitance increases with increasing volume of PEGDA-PEDOT. This also means that the charge storage capacity (CSC) of the Au film also improves with PEGDA-PEDOT coating.

The Applicant has further discovered that compared to commonly used (3-Glycidyloxypropyl)trimethoxysilane (GOPS) crosslinked PEDOT, the disclosed PEGDA-PEDOT shows consistently lower impedance and a higher CSC. When comparing bare PEGDA-PEDOT and bare Au, the PEGDA-PEDOT still shows a much lower interfacial impedance as manifested by the low frequency impedance. Experimental data related to these aspects is shown in FIGS. 18 and 19.

Figure 18:
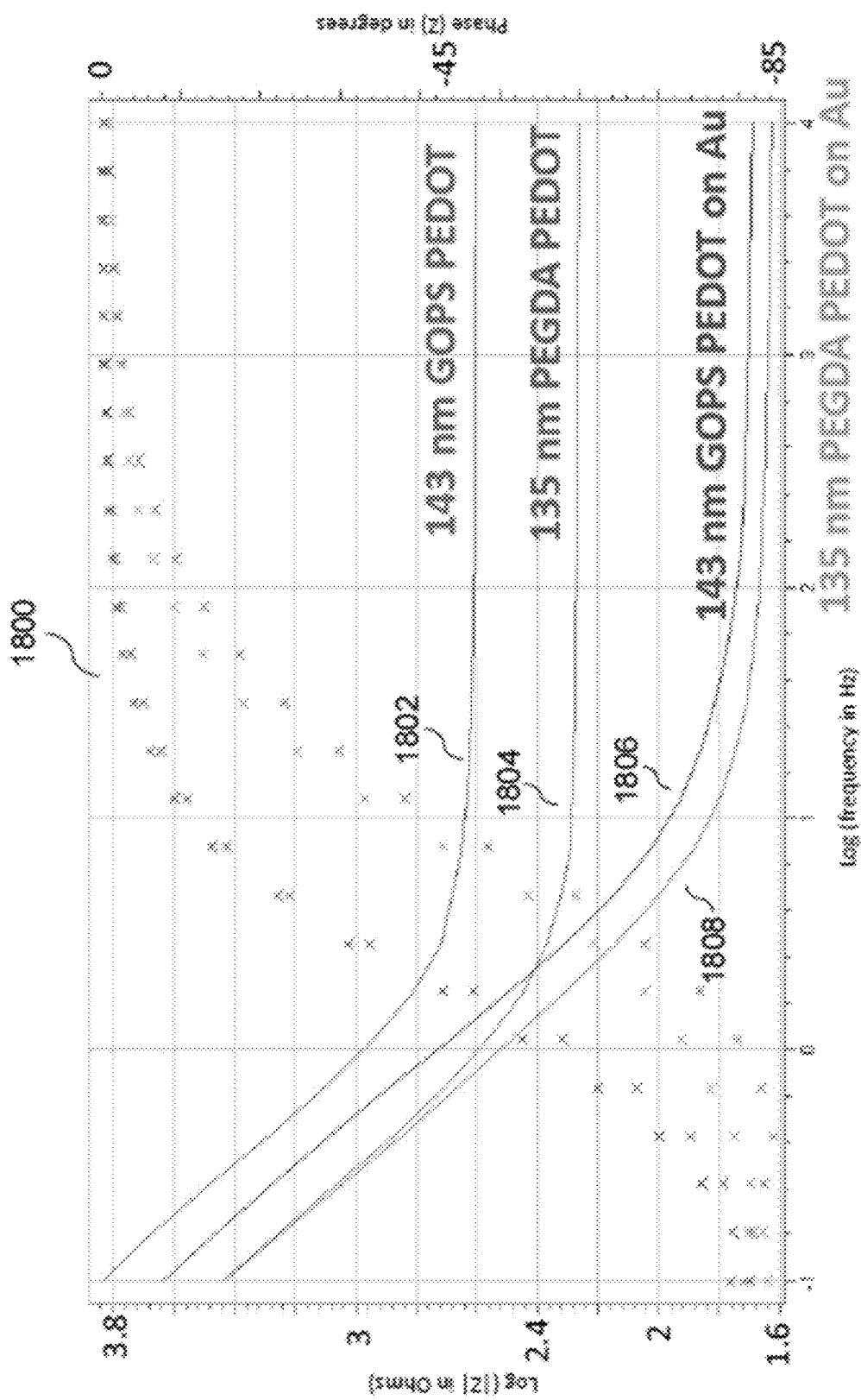
FIG. 18 is a graph 1800 of impedance versus frequency for an existing type of PEDOT film and a PEGDA-PEDOT film, according an embodiment of the present disclosure.

FIG. 18 is a graph 1800 of impedance versus frequency for a GOPS-PEDOT film and a PEGDA-PEDOT film based on EIS data. The graph 1800 shows frequency (Hz) in logarithmic scale on the x-axis and impedance (Ohms) in logarithmic scale on the y-axis. The graph 1800 includes a curve 1802 for a 143 nm GOPS-PEDOT, a curve 1804 for a 135 nm PEGDA-PEDOT film, a curve 1806 for an Au film with a 143 nm of GOPS-PEDOT coating, and a curve 1808 for an Au film with a 135 nm of PEGDA-PEDOT coating. As can be seen, the curve 1804 shows a much lower impedance than the curve 1802 and the curve 1808 shows a much lower impedance than the curve 1806 at lower frequencies. As such PEGDA-PEDOT film and Au film with a PEGDA-PEDOT coating show a lower interfacial impedance compared to GOPS-PEDOT and Au films with a GOPS-PEDOT coating.

Figure 19:
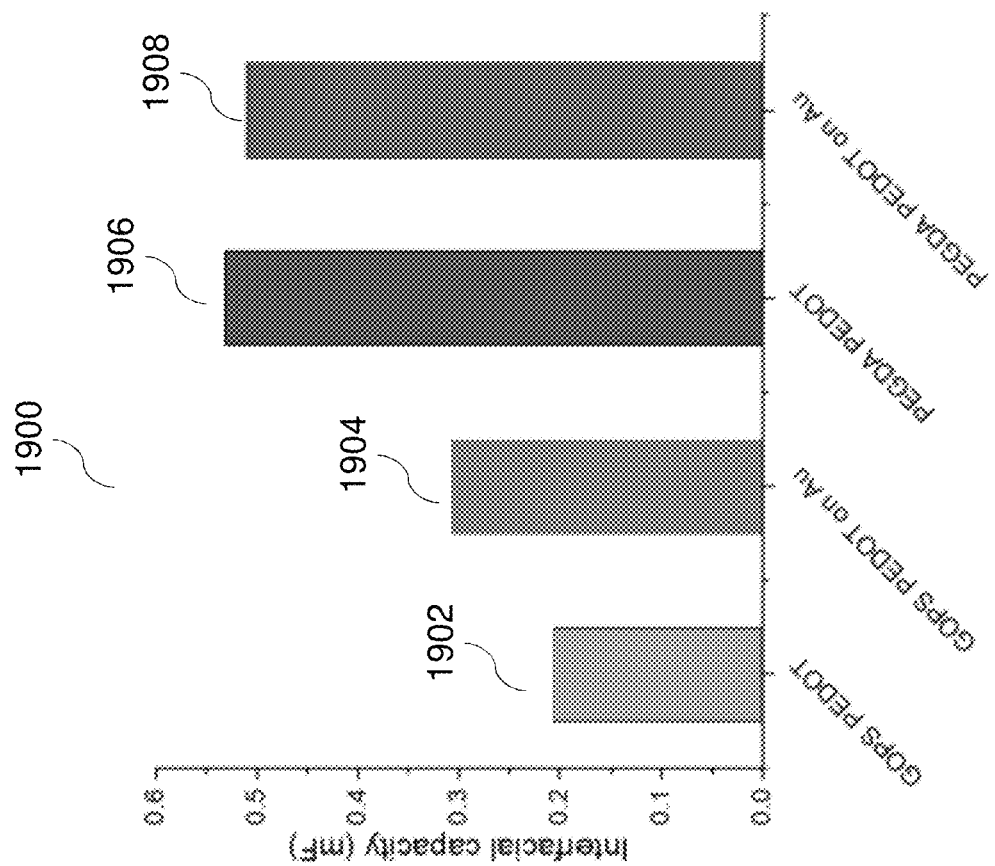
FIG. 19 is a chart 1900 of interfacial capacity for existing type of PEDOT film and a PEGDA-PEDOT film, according an embodiment of the present disclosure.

FIG. 19 is a bar chart 1900 showing interfacial capacity for various PEDOT films based on experimental data. The bar chart 1900 shows interfacial capacity in mF on y-axis and includes a bar 1902 for GOPS-PEDOT film, a bar 1904 for a PEGDA-PEDOT film, a bar 1906 for a GOPS-PEDOT coated Au film, and a bar 1908 for a PEGDA-PEDOT coated Au film on x-axis. As can be seen PEGDA-PEDOT related bars 1906 and 1908 exhibit consistently higher interfacial impedance compared to the GOPS related bars 1902 and 1904 respectively.

Figure 20:
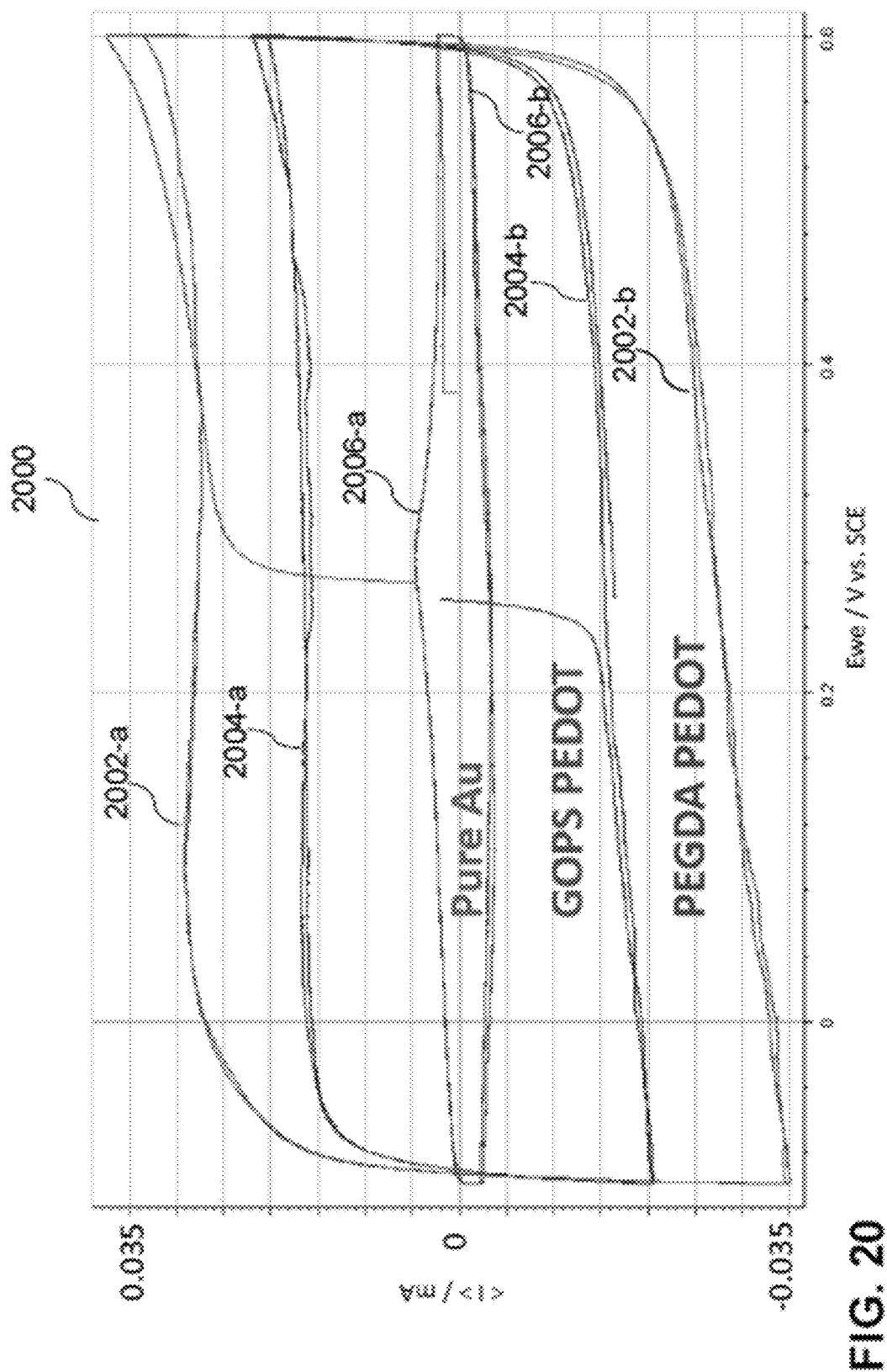
FIG. 20 is a graph 2000 of current versus voltage for an existing type of PEDOT film and a PEGDA-PEDOT film, according an embodiment of the present disclosure.

FIG. 20 is an example graph 2000 of current versus voltage for a GOPS-PEDOT film, a pure Au film, and a PEGDA-PEDOT film based on experimental data of cyclic voltammetry scans. The graph 2000 includes a scan indicated by 2002-a and 2002-b for a PEGDA-PEDOT film, a scan indicated by 2004-a and 2004-b for a GOPS-PEDOT film, and a scan indicated by 2006-a and 2006-b for a pure Au film. Like in a typical voltammetry scan, the graph 2000 shows a working electrode's potential (EWE) in volts vs. saturated calomel electrode (SCE) on x-axis and current in mA on y-axis. Those skilled in the art may appreciate that each scan starts with an open circuit potential and ramped up to approximately 0.6 V vs SCE and then ramped down to approximately −0.1 V vs SCE. It is clear that the PEGDA-PEDOT scan ramps up as 2002-a and ramps down as 2002-b, the GOPS-PEDOT scan ramps up as 2004-a and ramps down as 2004-b, and the pure Au scan ramps up 2006-a and ramps down as 2006-b. As can be seen, the PEGDA-PEDOT scan has a current of approximately in the range of 0.025 mA to 0.03 mA during ramp up as shown by 2002-b. The GOPS-PEDOT scan has a current of approximately in the range of 0.015 mA to 0.02 mA during ramp up as indicated by 2004-b. The pure Au scan has a current approximately in the range of 0 mA to 0.025 mA during ramp up as indicated by 2006-b. As such the PEGDA-PEDOT film shows highest current during ramp up. In other examples, the PEGDA_PEDOT film may also show the highest current during ramp down. As such the PEGDA-PEDOT film shows the highest current during the cyclic voltammetry scan which indicates a better conductivity.

Figure 21:
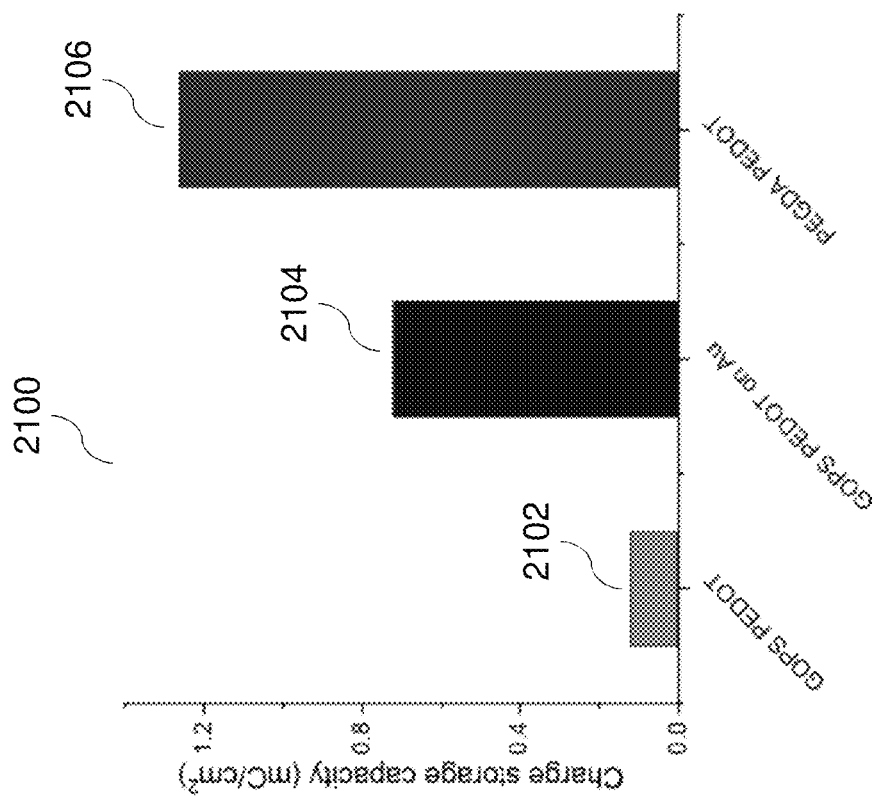
FIG. 21 is a chart 2100 of charge storage capacity for various PEDOT films.

FIG. 21 is a bar chart 2100 showing charge storage capacity for various PEDOT films based on experimental data. The bar chart 2100 shows charge storage capacity in $mC/cm^3$ on y-axis and includes a bar 2102 for GOPS-PEDOT film, a bar 2104 for a GOPS-PEDOT coated Au film, and a bar 2106 for a PEGDA-PEDOT coated Au film on x-axis. As can be seen the PEGDA-PEDOT bar 2106 exhibits the highest charge storage capacity of 1.2 $mC/cm^2$ compared to the GOPS-PEDOT bar 2102 with a CSC of approximately 0.1 $mC/cm^2$ and the GOPS-PEDOT on Au bar 2104 with a CSC of approximately 0.7 $mC/cm^2$.

Applicant has discovered that using PEGDA as the photocrosslinkable additive, PEDOT electrodes can be fabricated on elastomeric substrates with high conductivity and stretchability. When laminated onto human skin, such electrodes can be used to collect ECG and EMG signals. An example embodiment of this is shown in FIG. 22.

Figure 22:
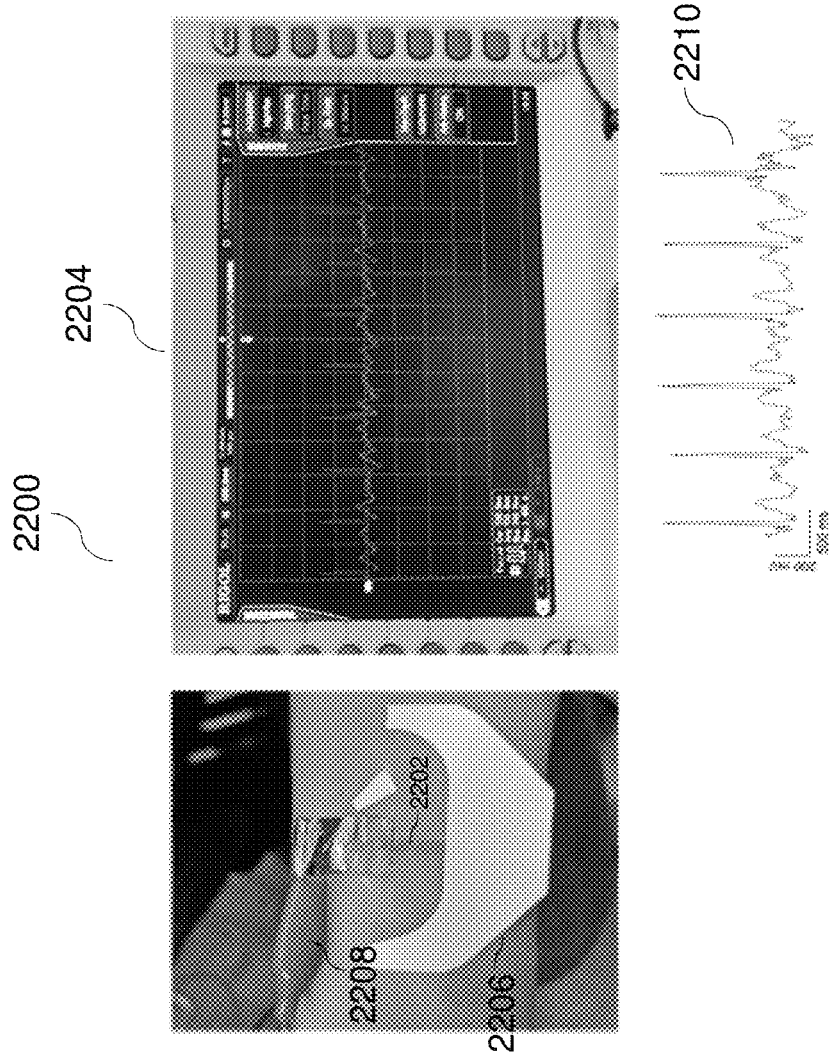
FIG. 22 illustrates an example application where a stretchable PEGDA-PEDOT electrode array according an embodiment of the present disclosure can be used.

FIG. 22 illustrates an example application where a stretchable PEGDA-PEDOT electrode array according an embodiment of the present disclosure can be used. The example application is an electrocardiography (ECG) which shows a stretchable PEGDA-PEDOT electrode 2202 attached to a patient's hand and the EMG screen 2204. In one example, the electrode 2202 may be attached to the patient's hand using a sticky tape 2206 and the signals from the electrode may be sensed using a banana clip 2208. The sensed ECG signals are shown as 2210.

Figure 23:
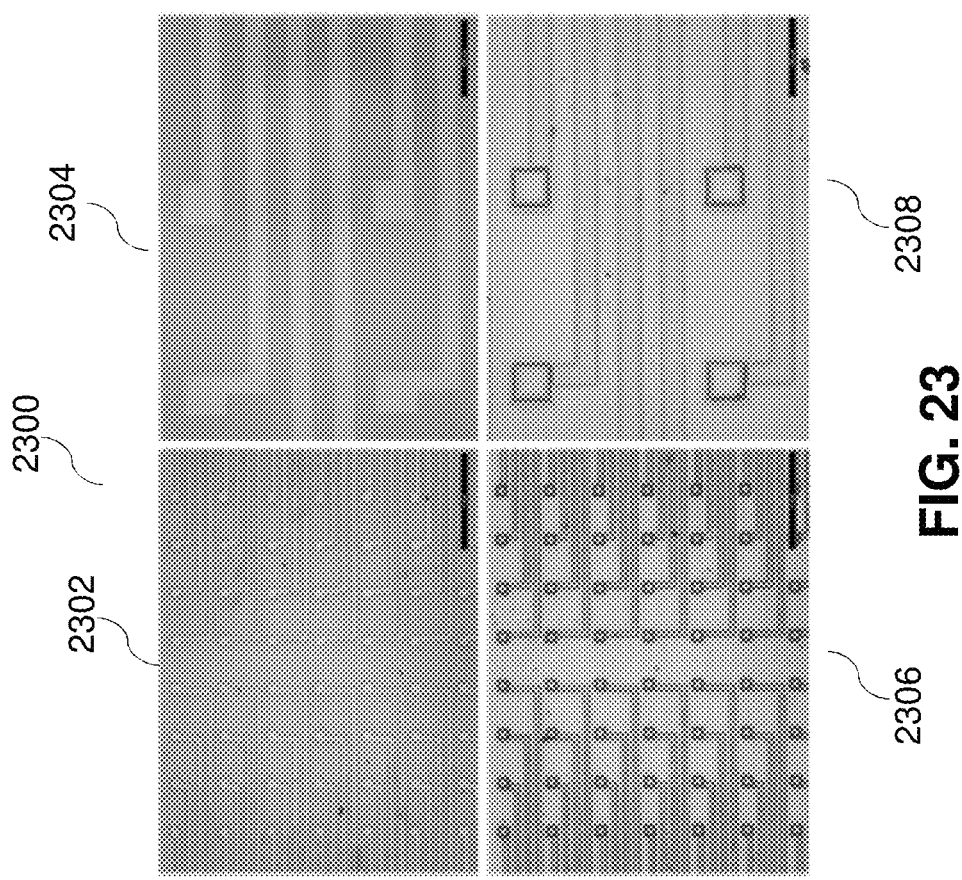
FIG. 23 illustrates an example microscopic image of a stretchable electrode array from PEDOT and SEBS encapsulation, according an embodiment of the present disclosure.

FIG. 23 illustrates an example microscopic images of a 64-channel stretchable electrode array 2300 from PEGDA-PEDOT and Styrene-ethylene-butylene-styrene (SEBS) encapsulation, according an embodiment of the present disclosure. Each electrode in the electrode array 2300 may be similar to the electrode 2202 shown in FIG. 22. The image 2302 shows the array 2300 without magnification without any SEBS encapsulation. The image 2304 shows the magnified array 2300 without any SEBS encapsulation. The image 2306 shows the array 2300 without magnification with SEBS encapsulation and the image 2308 shows the array 2300 with magnification and with SEBS encapsulation.

Figure 24:
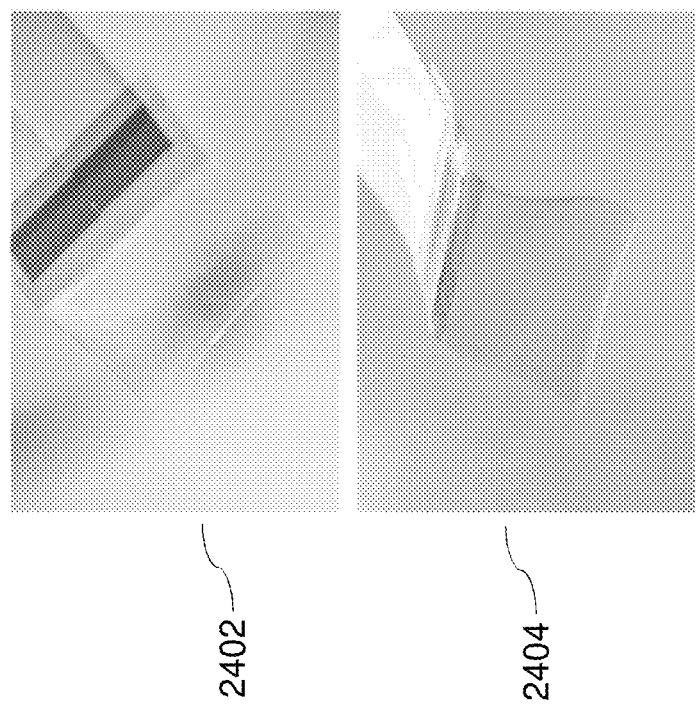
FIG. 24 illustrates digital images of the stretchable electrode array of FIG. 23, according an embodiment of the present disclosure.

FIG. 24 illustrates digital images 2402 showing a top view and 2404 showing an isometric view of the stretchable EMG electrode array 2300 of FIG. 23.

Figure 25:
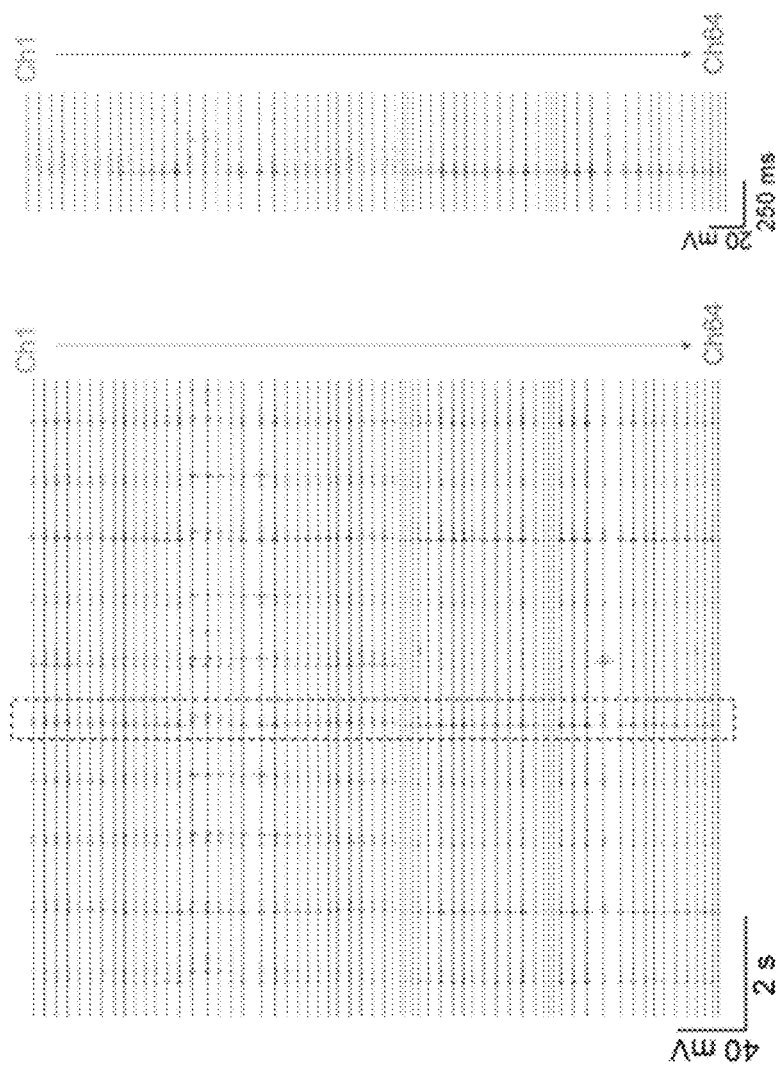
FIG. 25 illustrates example recorded EMG signals captured using the stretchable EMG electrode array of FIG. 23 and FIG. 24, according an embodiment of the present disclosure.

FIG. 25 illustrates example recorded EMG signals captured using the stretchable EMG electrode array 2300 of FIG. 23 or FIG. 24 or FIG. 25. As can be seen, the signals are received on 64 channels (channel 1 to channel 64).

Figure 26:
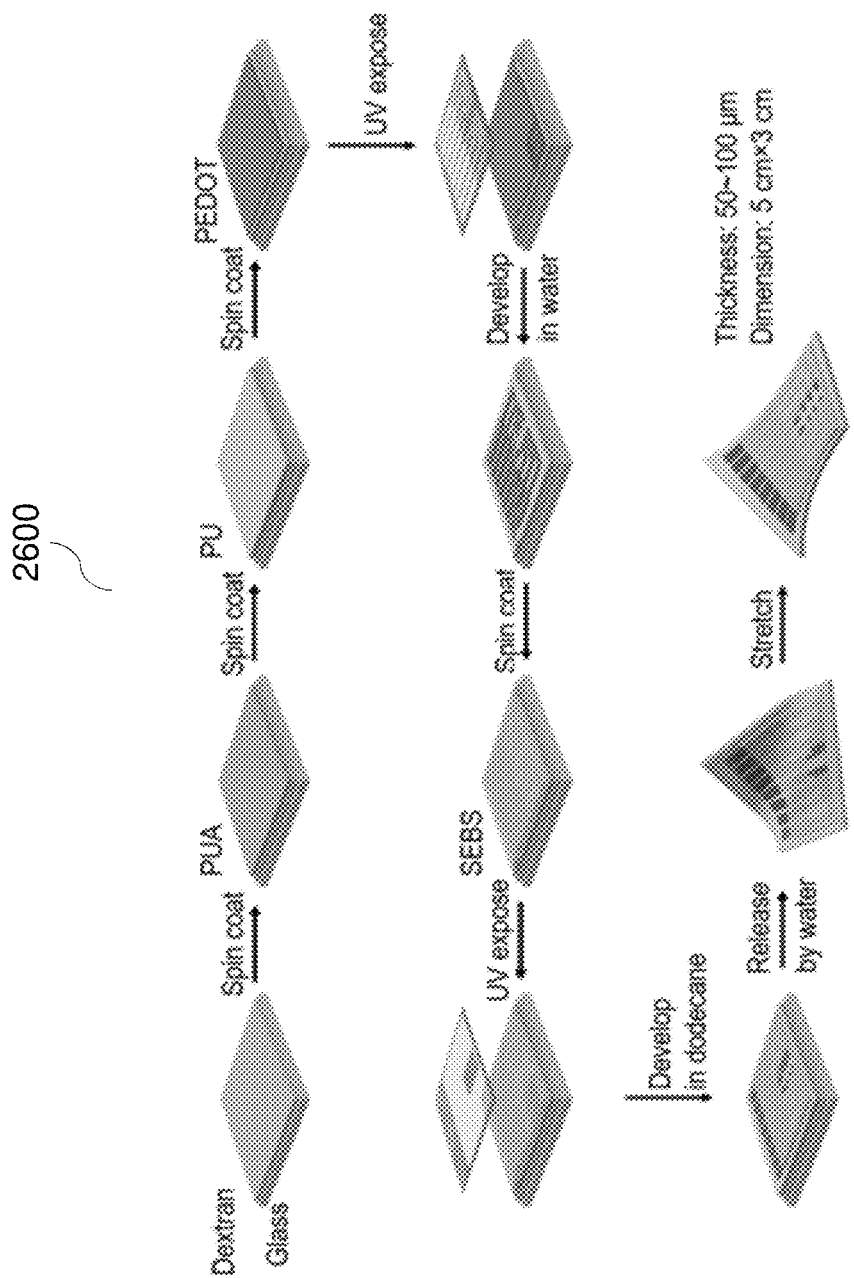
FIG. 26 illustrates an example fabrication process of a stretchable PEGDA-PEDOT electrode arrays, according to embodiments of the present disclosure.

FIG. 26 illustrates an example fabrication process 2600 of stretchable PEGDA-PEDOT electrode arrays, according to an embodiment of the present disclosure. Each electrode array may be similar to the electrode array 2300 in FIG. 23. In one example, the fabrication process of the stretchable electrode array may include but not limited to the following steps: (1) spin coating of dextran (Sigma-Aldrich) on glass to form a sacrificial layer (thickness ~200 nm), (2) spin coating of polyurethane acrylate (PUA, Dymax) as the carrier layer (thickness ~50 μm), (3) spin coating of polyurethane (PU, BASF) as the substrate layer (thickness ~5 μm), (4) spin coating of PEDOT/PEGDA (Agfa Orgacon ICP 1050/Sigma-Aldrich) as the electrode layer (thickness ~500 nm), (5) UV exposure of the PEDOT layer and development in water to make the electrode arrays and interconnects, (6) Methanol treatment for 30 s to boost the conductivity of PEDOT, (7) spin coating of styrene-ethylene-butylene-styrene (SEBS, Asahi Kasei) as the encapsulation layer (thickness ~5 μm), (8) UV exposure of the SEBS layer and development in dodecane to passivate the interconnects, (9) spray coating of silver nanowires (Ag NW) at the I/O pads before bonding PEDOT and a flat flex cable (FFC) using anisotropic conductive adhesives (ACA, 3M), and (10) releasing the entire device using water to dissolve dextran (total thickness 50-100 lateral dimension ~5 cm×3 cm). Notably, the overall thickness and bending stiffness of the entire device is mainly determined by the carrier PUA layer. Its thickness can be tuned by the spin coating speed and duration to yield thinner or thicker substrates. Although in the above mentioned steps dextran is spin coated on glass, in other examples, polyvinyl alcohol can also be spin coated on glass to form a sacrificial layer.

Figure 27:
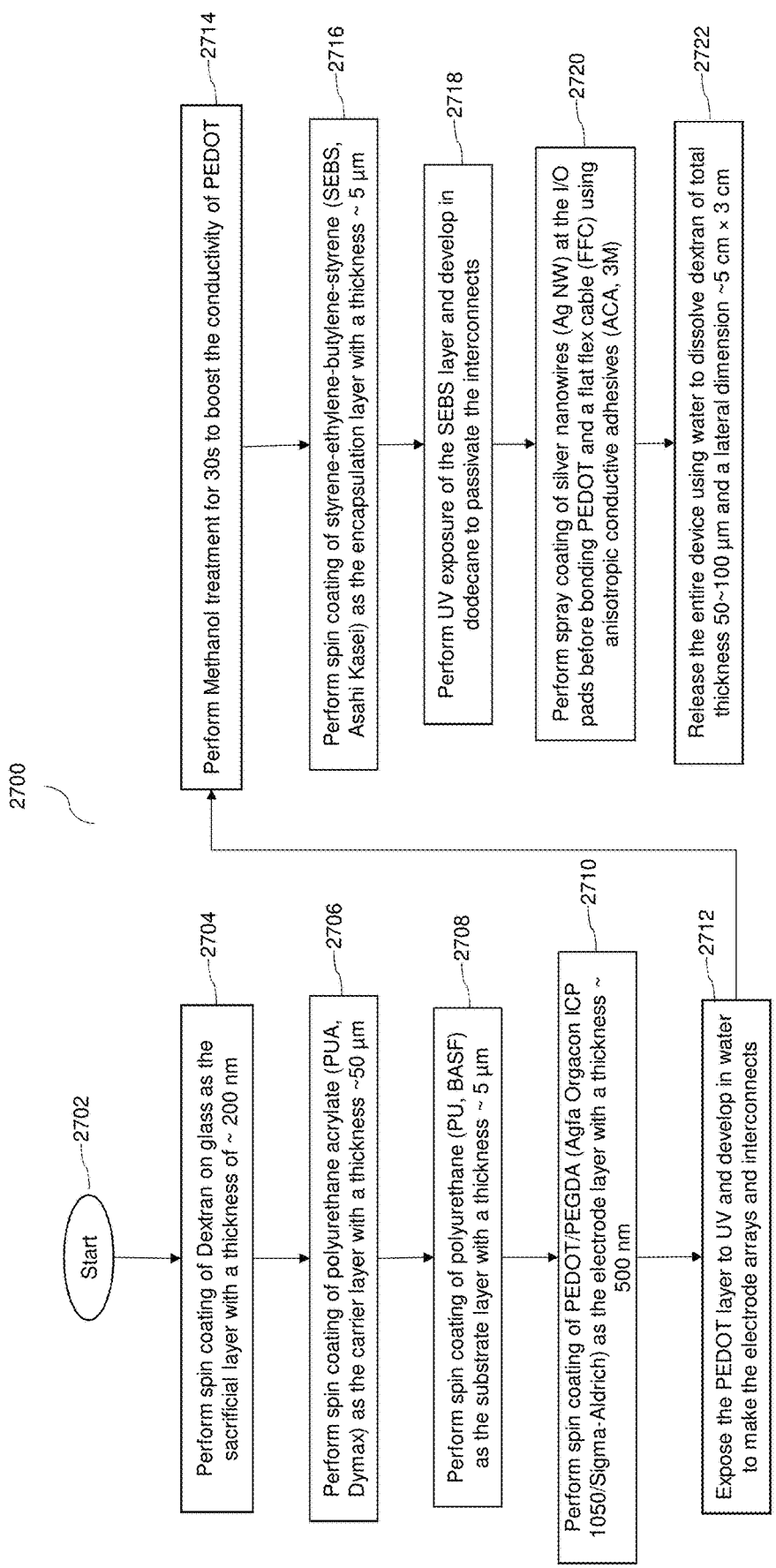
FIG. 27 illustrates an example flow diagram 2700 of making or fabricating the PEGDA-PEDOT electrode arrays.

FIG. 27 illustrates an example flow diagram 2700 of making or fabricating an PEGDA-PEDOT electrode array 2300 according to an embodiment as shown in FIG. 23 and as explained in FIG. 26. As shown, the blocks 2704 to 2722 follow the steps mentioned with respect to FIG. 6.

After starting at block 2702, the method proceeds to block 2704.

At block 2704, spin coating of dextran on glass as the sacrificial layer with a thickness of ~200 nm may be performed. The method proceeds to block 2706.

At block 2706, spin coating of polyurethane acrylate (PUA, Dymax) as the carrier layer with a thickness ~50 μm may be performed. The method proceeds to block 2708.

At block 2708, spin coating of polyurethane (PU, BASF) as the substrate layer with a thickness ~5 μm may be performed. The method proceeds to block 2710.

At block 2710, spin coating of PEDOT/PEGDA (Agfa Orgacon ICP 1050/Sigma-Aldrich) as the electrode layer with a thickness ~500 nm may be performed. The method proceeds to block 2712.

At block 2712, the PEDOT layer may be exposed to UV and developed in water to make the electrode arrays and interconnects. The method proceeds to block 2714.

At block 2714, a methanol treatment for 30 s to boost the conductivity of PEDOT may be performed. The method proceeds to block 2716.

At block 2716, a spin coating of styrene-ethylene-butylene-styrene (SEBS, Asahi Kasei) as the encapsulation layer with a thickness ~5 μm may be performed. The method proceeds to block 2718.

At block 2718, SEBS layer may be exposed to UV and developed in dodecane to passivate the interconnects. The method proceeds to block 2720.

At block 2720, spray coating of silver nanowires (Ag NW) at the I/O pads before bonding PEDOT and a flat flex cable (FFC) using anisotropic conductive adhesives (ACA, 3M) may be performed. The method proceeds to block 2722.

At block 2722, the entire device may be released using water to dissolve dextran of total thickness 50~100 μm and a lateral dimension ~5 cm×3 cm.

As used herein, the singular terms "a," "an," and "the" may include plural referents unless the context clearly dictates otherwise. Thus, for example, reference to an object may include multiple objects unless the context clearly dictates otherwise.

As used herein, the terms "substantially," "substantial," "approximately," and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claim(s). In addition, many modifications may be made to adapt a particular situation, material, composition of matter, method, operation or operations, to the objective, spirit and scope of the disclosure. All such modifications are intended to be within the scope of the claim(s) appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A film comprising:
   an electrically conductive polymer, wherein the electrically conductive polymer comprises poly(3,4-ethylenedioxythiophene):poly(styrenesulfonate) (PEDOT:PSS); and
   a cross-linked network intermixed with the electrically conductive polymer, wherein the crosslinked network is of poly(ethylene glycol) diacrylate (PEGDA),
   wherein a dry mass ratio of PEGDA versus PEDOT in the cross-linked network intermixed with the electrically conductive polymer is about 12% to about 65%, and
   wherein the intermixing of the cross-linked network with the electrically conductive polymer is configured to cause the film to have:
      an electrical conductivity of at least about 100 S/cm;
      a maximum tensile strain of at least about 10%; and
      a light transmittance at a wavelength of 550 nm of at least about 30%.

2. The film of claim 1, wherein the intermixing of the cross-linked network with the electrically conductive polymer is further configured to cause the film to have a higher interfacial capacity and a lower impedance compared to a 3-Glycidyloxypropyl)trimethoxysilane (GOPS) crosslinked poly(3,4-ethylenedioxythiophene):poly(styrenesulfonate) in a range of about 1-10 kHz.

3. The film of claim 2, wherein the film is further configured to sense an electrocardiographic or an electromyographic signal.

4. The film of claim 3, wherein the film further includes an Au film on which the electrically conductive polymer and intermixed cross-linked network is coated.

5. The film of claim 4, wherein the coating has a thickness in the range of 60 nm to 928 nm.

6. The film of claim 1, wherein the intermixing of the cross-linked network with the electrically conductive polymer is further configured to cause the film to have a current density of up to about 15 $\mu A/cm^2$.

7. The film of claim 1, wherein the intermixing of the cross-linked network with the electrically conductive polymer is further configured to cause the film to have a charge storage capacity of at least 1.2 $mC/cm^2$.

8. The film of claim 1, wherein a molar ratio of PSS and PEDOT as characterized by an atomic ratio of sulfur (S) in PSS and PEDOT is about 1.8 or less.

9. The film of claim 1, wherein a molar ratio of PSS and PEDOT as characterized by an atomic ratio of sulfur (S) in PSS and PEDOT is about 1.3 or less.

* * * * *